United States Patent
Schneidér et al.

(10) Patent No.: US 8,834,926 B2
(45) Date of Patent: Sep. 16, 2014

(54) MACROMOLECULAR DIFFUSION AND RELEASE FROM SELF-ASSEMBLED β-HAIRPIN PEPTIDE HYDROGELS

(75) Inventors: Joel P. Schneidér, Newark, DE (US); Monica C. Branco, Union, NJ (US); Darrin J. Pochan, Landenberg, PA (US); Norman J. Wagner, Newark, DE (US)

(73) Assignee: University of Delaware, Newark, DE (US)

( * ) Notice: Subject to any disclaimer, the term of this patent is extended or adjusted under 35 U.S.C. 154(b) by 911 days.

(21) Appl. No.: 12/533,708

(22) Filed: Jul. 31, 2009

(65) Prior Publication Data
US 2010/0034881 A1    Feb. 11, 2010

Related U.S. Application Data

(60) Provisional application No. 61/087,405, filed on Aug. 8, 2008.

(51) Int. Cl.
*A61K 9/06* (2006.01)
*A61K 38/10* (2006.01)
*A61K 38/16* (2006.01)
*A61K 9/00* (2006.01)
*A61K 47/36* (2006.01)

(52) U.S. Cl.
CPC . *A61K 9/06* (2013.01); *A61K 38/16* (2013.01); *A61K 38/10* (2013.01); *A61K 9/0019* (2013.01); *A61K 47/36* (2013.01)
USPC ........... 424/484; 530/300; 530/326; 530/350; 514/1.1; 514/773

(58) Field of Classification Search
None
See application file for complete search history.

(56) References Cited

U.S. PATENT DOCUMENTS

| 7,858,585 | B2 * | 12/2010 | Ozbas et al. | 514/21.4 |
| 2006/0025524 | A1 | 2/2006 | Schneider et al. | |
| 2007/0128175 | A1 * | 6/2007 | Ozbas et al. | 424/93.7 |
| 2009/0238788 | A1 | 9/2009 | Butterick et al. | |

FOREIGN PATENT DOCUMENTS

WO    WO 2007/059491 A2 *    5/2007

OTHER PUBLICATIONS

Vakkalanka et al. ("Temperature- and pH-sensitive terpolymers for modulated delivery of streptokinase," J. Biomater. Sci. Polymer Edn., 1996, vol. 8, No. 2, pp. 119-129).*
ExPASY ProtParam tool, data on streptokinase, printed Feb. 1, 2012 from http://web.expasy.org.*
Schneider, Joel P., et al.; "Responsive Hydrogels from the Intramolecular Folding and Self-Assembly of a Designed Peptide"; Journal Am. Chem. Soc.; Aug. 2002, pp. 15030-15037, vol. 124; US.
Branco, Monica C., et al.; "Macromolecular Diffusion and Release from Self-Assembled Beta-Hairpin Peptide Hydrogels"; J. Biomaterials; 2009, pp. 1339-1347, vol. 30; Amsterdam.
Butterick-Haines, Lisa A., et al.; "Controlling Hydrogelation Kinetics by Peptide Design for Three-Dimensional Encapsulation and Injectable Delivery of Cells"; PNAS May 8, 2007; vol. 104; pp. 7791-7796.
Rajagopal, Karthikan, et al.; "Self-Assembling Peptides and Proteins for Nanotechnological Applications"; Curr. Opinion in Struct. Bio.; 2004; vol. 14; pp. 480-486.
Ozbas, Bulent, et al.; "Salt-Triggered Peptide Folding and Consequent Self-Assembly Into Hydrogels with Tunable Modulus"; Macromolecules; 2004; vol. 37; pp. 7331-7337.
Pochan, Darrin J., et al.; "Thermally Reversible Hydrogels via Intramolecular Folding and Consequent Self-Assembly of de Novo Designed Peptide"; J. Amer. Chem. Soc.; 2003; vol. 125; pp. 11802-11803.
Rughani, Ronak, V., et al.; "Folding, Self-Assembly, and Bulk Material Properties of a De Novo Designed Three-Stranded β-Sheet Hydrogel"; Biomacromolecules; 2009; vol. 10; pp. 1295-1304.
Kretsinger, Juliana K . . . , et al.; "Cytocompatibility of Self-Assembled β-Hairpin Peptide Hydrogel Surfaces"; Biomaterials; Jan. 29, 2005, pp. 5177-5186, vol. 26; US.
Mart, Robert J., et al.; "Peptide-Based Stimuli-Responsive Biomaterials"; J; Softmatter; 2006, pp. 822-835, vol. 2; UK.
Chockalingam, Karuppiah, et al.; "Design and Application of Stimulus-Responsive Peptide Systems"; PEDS, Mar. 21, 2007; pp. 1-7; US.
Salick, Daphne A., et al.; "Inherent Antibacterial Activity of a Peptide-Based β-Hairpin Hydrogel"; J. Am. Chem. Soc.; 2007; vol. 129; pp. 14793-14799, US.
Ozbas, Bulent, et al.; "Reversible Stiffening Transition in β-Hairpin Hydrogels Induced by Ion Complexion"; J. Phys. Chem. B; 2007; vol. 111; pp. 13901-13908, US.
Yucel, Tuna, et al.; "Direct Observation of Early-Time Hydrogelation in β-Hairpin Peptide Self-Assembly"; Macromolecules; 2008; vol. 41; pp. 5763-5772, US.
Commissioner and Lee, Min Jung; "International Search Report"; Apr. 1, 2010; 16 pp; Korean Intellectual Property Office, Daejeon, Republic of Korea.

* cited by examiner

Primary Examiner — Christina Bradley
(74) Attorney, Agent, or Firm — RatnerPrestia

(57) ABSTRACT

A hydrogel for delayed release of an anionic macromolecule, wherein the hydrogel comprises the anionic macromolecule, 150 mM NaCl, and a peptide selected from the group consisting of SEQ ID NO:1 through SEQ ID NO:33 in an aqueous medium at a pH of 7.4; wherein the anionic macromolecule has an isoelectric point of at most 6.8; and wherein the hydrogel is capable of retaining at least 25% of the anionic macromolecule after 28-day extraction at 37° C. with a pH=7.4 BTP buffer containing 150 mM NaCl.

18 Claims, 10 Drawing Sheets

MACROMOLECULAR DIFFUSION AND RELEASE FROM SELF-ASSEMBLED β-HAIRPIN PEPTIDE HYDROGELS

CROSS REFERENCE TO RELATED APPLICATIONS

This application claims priority benefit of U.S. Provisional Patent Appln. No. 61/087,405, filed Aug. 8, 2008, the entirety of which is incorporated herein by reference for all purposes.

STATEMENT REGARDING FEDERALLY SPONSORED RESEARCH

Research leading to the disclosed invention was funded with funds from the National Institutes of Health under Grant R01 DE016386-01. Accordingly, the United States government has certain rights in the invention described herein.

BACKGROUND OF THE INVENTION

Macromolecules of various structures have proven useful as therapeutic agents for treating a variety of medical conditions. For example, advances in genomics, proteomics, and cell biology have led to the rapid development of small protein and antibody therapeutics. Growth factors, hormones, enzymes, cytokines, and monoclonal antibodies have been developed for a range of ailments such as cancer, autoimmune diseases, and metabolic disorders. Although the number of biopharmaceuticals approved and in advanced clinical testing continues to expand, there are challenges in preparing, storing and administering them. For example, the susceptibility of proteins to physical and chemical degradation during storage and proteolytic degradation upon administration can severely limit the therapeutic efficacy; the half lives, $t_{1/2}$, of many protein-based therapeutics range from only 2-100 minutes. Thus, methods of increasing the half-lives of therapeutic macromolecules during storage and/or under physiological conditions are of value.

SUMMARY OF THE INVENTION

In one aspect, the invention provides a hydrogel for delayed release of an anionic macromolecule. The hydrogel includes the anionic macromolecule, 150 mM NaCl, and a peptide selected from the group consisting of SEQ ID NO:1 through SEQ ID NO:33 in an aqueous medium at a pH of 7.4. The anionic macromolecule has an isoelectric point of at most 6.8 and the hydrogel is capable of retaining at least 25% of the anionic macromolecule after 28-day extraction at 37° C. with a pH=7.4 BTP buffer containing 150 mM NaCl.

In another aspect, the invention provides a modified-release hydrogel prepared by a method including shearing the hydrogel in the preceding paragraph under conditions sufficient to at least partially shear-thin the gel structure thereof, and subsequently allowing gelation to occur so as to form the modified-release hydrogel, wherein a diffusion coefficient of the anionic macromolecule in the modified-release hydrogel is less than that of the anionic macromolecule in the hydrogel of the preceding paragraph.

In yet another aspect, the invention provides a method of treating an animal that includes the step of introducing a hydrogel or a modified release hydrogel as described above into the body of an animal.

DETAILED DESCRIPTION OF THE INVENTION

Figure 1:
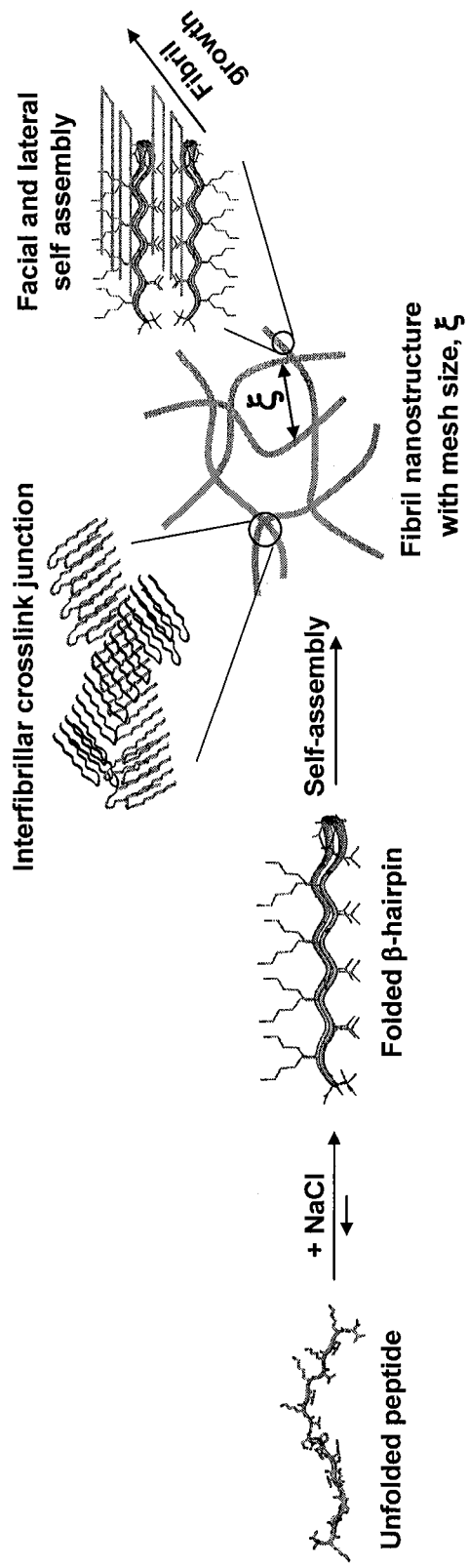
FIG. 1 shows a possible mechanism for the folding and self-assembly of MAX hydrogels.

The invention provides anionic macromolecule-containing hydrogels that provide long retention (i.e., very slow release, preferably none) of the macromolecules under physiologically compatible conditions. In particular, the anionic macromolecules include anionic biomolecules such as proteins and polysaccharides. These slow-release hydrogels are made by incorporating the anionic macromolecules into hydrogels formed by the self-assembly of certain peptides, referred to herein as MAX peptides and defined later herein.

The inventors have found that negatively charged macromolecules are slowed in release not only by being imbedded in the hydrogels, where the inventors found that smaller mesh size reduced macromolecule release, but also by some other interaction that the inventors believe may be based on the negative charge of the macromolecule. This effect was unexpected because it has been believed that the positive charge on the strands that constitute MAX peptide hydrogels is extensively screened by the presence of NaCl, allowing the gels to form.

The inventors have found that positively charged proteins and neutral antibodies diffuse within (and out of) MAX-based hydrogels relatively rapidly, and thus, are not strongly retained in the hydrogels. In contrast, negatively charged proteins have much lower mobility, and are much more strongly retained. Thus, delayed-release hydrogels may be prepared by incorporating anionic macromolecules in MAX-based hydrogels. Such anionic macromolecules may include therapeutic agents, and the hydrogels may be introduced into the body of an animal in need of treatment with that agent. They may be introduced in their gelled form or they may be sheared to break down the gel structure prior to treating the animal. Typically, but not necessarily, it may be applied by injecting through a syringe needle. In some cases, the act of ejecting the hydrogel from a syringe through a needle modifies the rate of release of the anionic macromolecule from the hydrogel.

Delayed Release Hydrogels

The delayed release hydrogels of the invention comprise anionic macromolecules incorporated in hydrogels formed by the self-assembly of MAX peptides. The hydrogels are physiologically compatible, having a pH of 7.4 and containing 150 mM NaCl. Unless referring to a specific experiment, where the pH values and concentrations of ingredients are exact within experimental uncertainty, a pH value of 7.4 should be understood to encompass physiologically acceptable variations around that value and an NaCl concentration of 150 mM NaCl should be understood to encompass physiologically acceptable variations around that value, provided that the desired gel properties are maintained. Thus, the pH value may vary at least within a range of 7.35 to 7.45 and the NaCl concentration may vary at least within in a range of 140 to 160 mM, provided that the desired gel properties are maintained. The pH is maintained with a suitable buffer, typically a nonionic buffer such as bis-tris propane (BTP). As used herein, the term "physiological buffer" will be used to designate an aqueous solution buffered to pH=7.4, containing 50 mM BTP and 150 mM NaCl. The MAX peptide content of hydrogels according to the invention may be at least 0.1 wt %, or at least 0.3 wt %, or at least 0.5 wt %. There is no particular upper limit to the MAX peptide content, but typically it will be at most 5.0 wt %, or at most 4.0 wt %, or at most 3.0 wt %. Commonly, it is about 2.0 wt %. The anionic macromolecule (or a mixture of anionic macromolecules) may typically be present at a content of at least 1 nM, or at least 1 µM. There is no particular upper limit to the anionic macromolecule content, but typically it will be at most 1 M, or at most at most 1 mM. A concentration of about 100 µM may commonly be used.

The hydrogel is capable of retaining at least 25% of the anionic macromolecule after 28-day extraction at 37° C. with physiological buffer. In some embodiments, at least 50%, or at least 75%, or at least 90% is retained. The diffusion coefficient for the anionic macromolecules in hydrogels according to the invention is at most $60 \times 10^{-8}$ cm$^2$/sec, typically at most $30 \times 10^{-8}$ cm$^2$/sec. It maybe as low as $0.5 \times 10^{-8}$ cm$^2$/sec.

Hydrogels according to the invention typically have a storage modulus G' of at least 100 Pa, more typically at least 500 Pa, still more typically at least 1000 Pa, and most typically at least 2000 Pa. In some embodiments, the storage modulus is at least 5000 Pa.

In some embodiments of the invention, a modified-release hydrogel is prepared by a method comprising shearing a hydrogel as described above under conditions sufficient to at least partially shear-thin the gel structure, and then allowing gelation to occur so as to form the modified-release hydrogel. In some embodiments of the invention, the diffusion coefficient of the anionic macromolecule in the modified-release hydrogel is less than that of the anionic macromolecule in the hydrogel prior to shearing. In some embodiments, the diffusion coefficient of the anionic macromolecule in the modified-release hydrogel is less than 70% of the diffusion coefficient in the gel prior to shearing, or less than 50% of that value. In some embodiments, the modified-release hydrogel is able to retain less of the anionic macromolecule after 28-day extraction at 37° C. with physiological buffer than does the hydrogel prior to shearing.

MAX Peptides

Suitable MAX peptides include any of a class of self-assembling beta-hairpin peptides that undergo triggered hydrogelation in response to physiological pH and salt conditions (pH 7.4, 150 mM NaCl) to form mechanically rigid, viscoelastic gels. As used herein, the term MAX peptide(s) means a peptide selected from the following group.

|  |  | (SEQ ID NO: 4) |
|---|---|---|
| HPL8 | VKVKVKVK V$^D$PPT KVEVKVKV-NH$_2$ | |

|  |  | (SEQ ID NO: 6) |
|---|---|---|
| MAX1 | VKVKVKVK V$^D$PPT KVKVKVKV-NH$_2$ | |

|  |  | (SEQ ID NO: 7) |
|---|---|---|
| MAX2 | VKVKVKVK V$^D$PPT KVKTKVKV-NH$_2$ | |

|  |  | (SEQ ID NO: 8) |
|---|---|---|
| MAX3 | VKVKVKTK V$^D$PPT KVKTKVKV-NH$_2$ | |

|  |  | (SEQ ID NO: 9) |
|---|---|---|
| MAX4 | KVKVKVKV K$^D$PPS VKVKVKVK-NH$_2$ | |

|  |  | (SEQ ID NO: 10) |
|---|---|---|
| MAX5 | VKVKVKVK V$^D$PPT KVKEKVKV-NH$_2$ | |

|  |  | (SEQ ID NO: 11) |
|---|---|---|
| MAX6 | VKVKVKVK V$^D$PPT KVKCKVKV-NH$_2$ | |

|  |  | (SEQ ID NO: 12) |
|---|---|---|
| MAX7 | VKVKVKVK V$^D$PGT KVKVKVKV-NH$_2$ | |

|  |  | (SEQ ID NO: 13) |
|---|---|---|
| MAX8 | VKVKVKVK VP$^D$PT KVKVKVKV-NH$_2$ | |

|  |  | (SEQ ID NO: 1) |
|---|---|---|
| MAX9 | VKVKVKVK VPPT KVKVKVKV-NH$_2$ | |

|  |  | (SEQ ID NO: 14) |
|---|---|---|
| MAX10 | VKVKVKVK V$^D$P$^D$PT KVKVKVKV-NH$_2$ | |

|  |  | (SEQ ID NO: 15) |
|---|---|---|
| MAX11 | VKVKKCK V$^D$PPT KVCKVKV-NH$_2$ | |

|  |  | (SEQ ID NO: 16) |
|---|---|---|
| MAX12 | VKVKCKVK V$^D$PPT KVCVKVKV-NH$_2$ | |

|  |  | (SEQ ID NO: 17) |
|---|---|---|
| MAX14 | VKVKVCVK V$^D$PPT CVKVKVKV-NH$_2$ | |

|  |  | (SEQ ID NO: 18) |
|---|---|---|
| MAX15 | VKVKVCVK V$^D$PPT KVKVCVKV-NH$_2$ | |

|  |  | (SEQ ID NO: 19) |
|---|---|---|
| MAX16 | VKVKVKVC V$^D$PPT KVKVCVKV-NH$_2$ | |

|  |  | (SEQ ID NO: 20) |
|---|---|---|
| MAX17 | RGDVKVKVKVK V$^D$PPT KVKVKVKVRGD-NH$_2$ | |

|  |  | (SEQ ID NO: 21) |
|---|---|---|
| MAX18 | VKVEVKVE V$^D$PPT KVEVKVEV-NH$_2$ | |

-continued

```
MAX19    VKVKVKVKVK V^DPPT KVKVKVKVKV-NH_2        (SEQ ID NO: 22)

MAX20    VKVKVKVK YNGT KVKVKVKV-NH_2              (SEQ ID NO: 2)

MAX21    VKVKVK V^DPPT KVKVKV-NH_2                (SEQ ID NO: 23)

MAX24    VXVXVXVX V^DPPT XVXVXVXV-NH_2            (SEQ ID NO: 24)
         X = Ornithine MAX25    VXVXVXVX V^DPPT XVXVXVXV-NH_2            (SEQ ID NO: 25)
         X = Diaminobutyric acid MAX26    VXVXVXVX V^DPPT XVXVXVXV-NH_2            (SEQ ID NO: 26)
         X = Diaminopropionic acid

MAX28    VRVRVRVR V^DPPT RVRVRVRV-NH_2            (SEQ ID NO: 27)

MAX29    VKVKVKVKVRGDKVKVKVKV-NH_2                (SEQ ID NO: 3)

MAX30    XKXKXKXK V^DPPT KXKXKXKX-NH_2            (SEQ ID NO: 28)
         X = Aminoisobutyric acid MAX31    XKXKXKXK V^DPPT KXKXKXKX-NH_2            (SEQ ID NO: 29)
         X = Norvaline MAX32    XKXKXKXK V^DPPT KXKXKXKX-NH_2            (SEQ ID NO: 30)
         X = Norleucine

MAX33    FKFKFKFK V^DPPT KFKFKFKF-NH_2            (SEQ ID NO: 31)

MAX34    IKIKIKIK V^DPPT KIKIKIKI-NH_2            (SEQ ID NO: 32)

MAXX_1   (VK)_m V^DPPT (KV)_n-NH_2                (SEQ ID NO: 33)
         m = 1-100,
         n = 1-100

MAXX_6   (VK)_m YNGT (KV)_n-NH_2                  (SEQ ID NO: 5)
         m = 1-100,
         n = 1-100
```

Each m and n may independently be from 1-100 and m may or may not equal n. Amino acids having D stereochemistry are indicated herein by a superscript before the D amino acid, and thus, $^{D}$P is D-proline.

These peptides, and methods of making them, are described in Branco et al. Biomaterials, 2009, 30, 1339 and copending U.S. patent appln. Ser. No. 10/900,344 to Schneider et al. and Ser. No. 11/598,763 to Ozbas et al., all of which are incorporated herein by reference for all purposes.

MAX1, a typical peptide useful for making hydrogels according to the invention, consists of 20 amino acids, eight of which are lysine residues. When dissolved in low ionic strength (≤10 mM NaCl) aqueous solutions at pH 7.4, MAX1 remains unfolded and soluble mainly due to electrostatic repulsion between the positively charged lysine side chains. However, when a physiologically relevant concentration of NaCl (150 mM) is added, this charge is effectively screened and the peptide folds into an amphiphilic β-hairpin. The hairpin is composed of two β-strands of alternating lysine and valine residues connected by a four residue type II' β-turn, as depicted in FIG. 1. The lysine-rich face of the hairpin is hydrophilic and the valine-rich face is hydrophobic. The folded hairpin is highly amenable to self-assembly, ultimately forming a network of β-sheet rich fibrils. MAX1 self-assembles laterally, forming a network of hydrogen bonds along the long axis of a given fibril. The peptide also assembles facially, burying the hydrophobic valine-rich face from water, forming a bilayer. Thus, each fibril is composed of a bilayer of hairpins where the surface of the fibril displays positively charged lysine side chains. Transmission electron microscopy (TEM) and small angle neutron scattering (SANS) show that in the long portions of the fibrils, hairpins facially assemble in a manner in which all of their β-strands are in register with each other and the maximal amount of valine side chain surface area is shielded from water. However, imperfections in this mechanism can occur where the face of one hairpin is rotated relative to its partner in the bilayer. This results in a site for nascent fibril growth in a new three-dimensional direction and results in formation of an interfibril crosslink as shown in FIG. 1. In addition to the interfibril crosslinks, at sufficient peptide concentrations, entanglements of fibrils also contribute to the mechanical rigidity of the gel.

A convenient way to control mesh size of the gel is simply to increase the peptide concentration used to prepare the gel. The additional peptide leads to the formation of more fibrils that entangle and crosslink into the network, providing gels with smaller mesh sizes.

A second method to control mesh size involves modulating the rate of gel formation. In general, the kinetics of peptide folding and self-assembly dictates the number of crosslinks that are formed during the material formation process. In turn, the number of crosslinks directly influences the mechanical rigidity and mesh size of the gel. Slow kinetics of assembly lead to less rigid gels with fewer crosslinks and a larger average mesh size. Fast kinetics lead to a more rigid gel containing more crosslinks and a smaller average mesh size. Smaller mesh sizes will more effectively hinder macromolecular diffusion during delivery.

For the β-hairpin peptides described herein, it is possible to control the folding and self-assembly kinetics to form hydrogels with different mesh sizes. For example, making changes to the peptide sequence can directly influence the rate of peptide folding and self-assembly. HPL8 is a design descendent of MAX1 containing a point substitution on the hydrophilic face of the hairpin where one lysine at position 15 is replaced with a glutamic acid. This simple substitution reduces the overall charge state of the peptide to about +7 at physiological pH. For comparison, MAX1 contains eight lysine residues and an N-terminal ammonium group leading to a charge state of about +9 at pH 7.4. Since HPL8 has a lower amount of positive charge to be screened, it folds and self-assembles much faster than MAX1 in response to similar buffer conditions. Therefore, at identical peptide concentrations and solution conditions, HPL8 forms gels that are more rigid and contain more crosslinks, resulting in smaller mesh sizes. The inventors have found that hydrogel mesh size can be modulated by varying either the peptide sequence or the peptide concentration, or both, and that mesh size directly influences the release profiles of incorporated macromolecules.

Anionic Macromolecules

As used herein, the terms "anionic" or "negatively charged" as applied to macromolecules means that the macromolecule's isoelectric point (pI) is less than the pH of the system (7.4). Similarly, a "cationic" or "positively charged" macromolecule has an isoelectric point greater than 7.4, and a "neutral" macromolecule has an isoelectric point of ~7.4.

Suitable anionic macromolecules for incorporation in hydrogels according to the invention include macromolecules soluble in a pH=7.4 aqueous buffer solution and having a molecular weight of at least 5 kD (kilodaltons), or at least 10 kD, or at least 20 kD. There is no known upper limit on molecular weight, but typically it will be at most 1,000 kD, or at most 500 kD, or at most 200 kD. The isoelectric point (pI) of the anionic macromolecule is less than 7.0, or at most 6.8. or at most 6.5, or at most 6.0, or at most 5.5, or at most 5.0, or at most 4.5. In general, lower pI produces longer retention (i.e., longer delayed release). Suitable anionic macromolecules include polysaccharides (for example, modified dextrans) bearing carboxylate, sulfonate, phosphonate or other moieties conferring anionic charge, as well as some proteins, DNA and RNA.

Use of Delayed Release Hydrogels

The hydrogels of this invention may be of particular value for treating an animal for a medical condition. If the anionic macromolecule is a therapeutic agent, for example an anionic protein, the hydrogel may conveniently be applied by injection through a syringe needle, allowing minimally invasive deposition of the therapeutic agent at a desired localized site. Such treatment may be used for a mammal, a bird, a reptile, or any animal. Treatment of humans may be of particular value. In an animal, final release of all of the anionic macromolecule may depend upon destruction of the hydrogel structure due to enzymatic degradation of the MAX molecules, a process that may take several months to complete.

Detailed examples will now be presented, illustrating the very high level of retention of anionic macromolecules in MAX hydrogels according to the invention, as contrasted with the lower values obtained in MAX hydrogels incorporating neutral or cationic macromolecules.

EXAMPLES

MAX Gels Containing FITC-Dextran or Lactoferrin
Materials and Methods

Bis-tris propane (BTP), sodium chloride (NaCl), fluorescein isothiocyanate dextran (FITC-dextran) and lactoferrin were purchased from Sigma-Aldrich. The FITC-dextrans had molecular weights of 19,400 D (commercially available as 20 kD), 75,090 D (70 kD), and 170,000 D (150 kD).

MAX1 and HPL8 peptides were synthesized according to the method described in Schneider, J. P., et al., *Responsive hydrogels from the intramolecular folding and self-assembly of a designed peptide*. Journal of the American Chemical Society, 2002, 124(50): p. 15030-15037. Briefly, peptides were synthesized on RINK amide resin using standard Fmoc-protocol with HCTU activation on an automated ABI 433A peptide synthesizer. Cleavage and side-chain deprotection of the dry resin-bound peptides was performed with a trifluoroacetic acid (TFA): thioanisole: ethanedithiol: anisole (90:5:3:2) cocktail for 2 hr under $N_2$ atmosphere. Filtration followed by ether precipitation yielded crude peptides. Purification of the crude peptides was performed by RP-HPLC using a preparative Vydac C18 peptide column with a flow rate of 8 mL/min. Peptide is injected onto the column under isocratic conditions. MAX1 gradient: 0% B for 2 min, then a linear gradient from 0 to 18% B over 4 min, then 18% to 100% B over 164 min. Peptide elutes at 29 min. MS (ESI) m/z: 1115.4 [(M+2H)$^{2+}$, calculated: 1115.9]. HPL8 gradient: 0% B for 2 min, then a linear gradient from 0 to 24% B over 4 min, then 24% to 100% B over 152 min. Peptide elutes at 30 min. MS (ESI) m/z: 1115.9 [(M+2H)$^{2+}$, calculated: 1116.5]. Elutants for RP-HPLC consisted of Standard A (0.1% TFA in water) and Standard B (90% acetonitrile, 9.9% water, 0.1% TFA). Lyophilized purified peptides were dissolved in water at 1 mg/mL and re-lyophilized twice before being used for hydrogelation.

Dynamic Oscillatory Rheology

Oscillatory rheology experiments were performed on a Paar Physica MCR 500 rheometer using 25 mm diameter stainless steel parallel plate geometry. For the rheological measurements, gels were prepared directly on the rheometer plate in the following manner. For both MAX1 and HPL8 gels of varying weight percent, peptide stock solutions were first prepared in glass vials by dissolving 2, 4, and 8 mg of each peptide in 200 μL of sterile, chilled water resulting in three stock solutions per peptide. To each stock was added 200 μL of chilled BTP buffer (100 mM, pH 7.4) containing 300 mM NaCl. To prepare gels that directly encapsulate the dextran molecules, 200 μL of chilled BTP buffer (100 mM, pH 7.4) containing 300 mM NaCl and 1.2 mg/mL of the respective FITC-dextran was added to the stock solution. This results in 0.5, 1.0, and 2.0 wt % gels, respectively, at a final total volume of 400 μL. Then 300 μL of the resulting solution was quickly added to the rheometer plate, which was pre-equilibrated at 5° C. The parallel plate tool was then lowered to a gap height of 0.5 mm and the temperature was ramped linearly to 25° C. to initiate gelation. Initially, a dynamic time sweep was performed to measure the storage (G') and loss (G") modulus at a frequency of 6 rad/sec and 0.2% strain as a function of time until a plateau modulus was reached. A dynamic frequency sweep (0.1 to 100 rad/sec at constant 0.2% strain) was then performed, followed by a dynamic strain sweep (0.1 to 1000% strain at constant 6 rad/sec), which was used to verify that the former measurements were within the linear viscoelastic regime.

FRAP Diffusion Measurements

For the FRAP experiments, 1, 2, or 4 mg of the appropriate peptide was fully dissolved in 100 μL of sterile, chilled water to prepare separate stock solutions. Then, 75 μL of each stock was added to a separate well of a Lab-Tek II Chamber 8 well plate. To each well, 75 μL of BTP buffer (100 mM, pH 7.4) containing 300 mM NaCl was added. Samples were carefully agitated to cover the bottom of the well and to initiate hydrogelation, resulting in 0.5, 1.0, and 2.0 wt % gels, respectively, at a final total volume of 150 μL. Stock solutions of 20, 70, and 150 kD FITC-dextran macromolecules were prepared fresh at a concentration of 1.05 mg/ml of FITC-dextran in physiological buffer prior to each FRAP experiment. Twenty-four hours after gel preparation, 200 μL of this solution was added to the top of the hydrogels to yield a final dextran concentration of 0.6 mg/ml (37 μM with respect to the fluorescein groups for all dextrans). (Other experiments not shown here indicated this concentration to provide optimal fluorescence within the linear region of fluorescence intensity for the FRAP experiments.)

The diffusion coefficients of the FITC-dextrans were measured using the FRAP method with laser scanning confocal microscopy (LSCM). Measurements were taken on a Zeiss 510 LCM confocal microscope with a 20× magnification objective and an argon ion laser set at 488 nm with 50% power. The 20× objective lens has a cylindrical bleaching volume in which diffusion is avoided in the third dimension. Briefly, for a typical FRAP experiment, the confocal microscope scans an image along the xy plane of the sample. The center of a 512×512 pixel image (30 μm above the bottom of the plate) was chosen as the z-component of the confocal image. A circle of a diameter of 115 pixels (pixel=0.9 μm) was selected as the bleaching area. The area was monitored by 15 pre-bleach scanned images at low laser intensity (2%), then bleached with 50 iterations (about 10 seconds total) at 100% laser intensity, and followed by detection of the fluorescence recovery again at low intensity. A total of about 500 image scans (<1 sec each) were collected for each sample. FRAP experiments of the hydrogels were performed after 24 hours of incubation with the 20 kD and 70 kD dextran solutions, and after 48 hrs of incubation with the 150 kD dextran solution to ensure that the respective macromolecules had diffused homogeneously throughout the gel. Homogeneity was verified visually by monitoring the color change of the gel as the macromolecules diffused into the matrix. All experiments were performed at 25° C.

FRAP Data Analysis

Two-dimensional lateral self-diffusion coefficients (D) were determined by first collecting normalized fluorescence recovery curves for each macromolecule in both MAX1 and HPL8 gels of differing weight percent. For each experiment, a normalized fluorescence recovery curve, f(t), was obtained according to Equation 1 where F(t) is the observed fluorescence after photobleaching and $F_{in}$ is the background fluorescence intensity obtained prior to photobleaching.

$$f(t) = 1 + \frac{1}{R}\left(\frac{F(t) - F_{in}}{F_{in}}\right) \quad [1]$$

The parameter, R, is the mobile fraction of the macromolecules in the network. Due to interactions between the macromolecules and the hydrogel network, a portion of the fluorescent macromolecules remain immobile, and this immobile fraction has to be considered in the calculation of the normalized fluorescence values. R is determined by Equation 2 where $F_\infty$ is the fluorescence intensity of the bleached spot at the end of the experiment and $F_0$ is the fluorescence intensity of the bleached spot immediately after bleaching.

$$R = \frac{F_\infty - F_0}{F_{in} - F_0} \quad [2]$$

The self-diffusion coefficient (D) of a given FITC-dextran was obtained by fitting the normalized fluorescence recovery curve (f(t)) with Equation 3.

$$f(t) = \sum_{n=0}^{n=\infty} \frac{(-b)^n}{n!} \frac{1}{1 + n[1 + (2t/\tau_D)]} \quad [3]$$

The bleaching parameter, b, was also fit, and describes the efficiency of bleaching. It is dependent on the intensity of the laser beam, the bleach time, and the sensitivity of the fluorescent molecule for bleaching. Importantly, $\tau_D$ (the characteristic diffusion time) was also fit. The 2-D lateral self-diffusion coefficient, D, was then calculated from $\tau_D$ according to Equation 4.

$$D = \frac{\omega^2}{4\tau_D} \quad [4]$$

where $\omega$ is the radius of the Gaussian bleached spot (set constant at 51.75 μm).

Determination of Macromolecule Hydrodynamic Radius

Hydrodynamic diameters ($d_H$) were determined for each of the commercially available FITC-dextrans according to Equation 5, where $k_B$ is Boltzmann's $$d_H = \frac{k_B T}{3\pi \eta D} \quad [5]$$

constant, T is the temperature (25° C., 298° K), η is the zero-shear viscosity of the aqueous solution (0.001 Pa·s), and D is the diffusion coefficient of each macromolecule measured in physiological buffer in the absence of gel. Diffusion coefficients were measured according to the experimental protocol given in Sections 2.3 and 2.4. Macromolecule diameters are 6.2, 9.3, and 12.1 nm for the 20, 70, and 150 kD FITC-dextrans, respectively. The measured values of $d_H$ are in good agreement with those reported in the literature using FRAP and other established techniques.

Release Studies

For the bulk release studies, MAX1 and HPL8 peptide stock solutions were first prepared in glass vials by dissolving 1.5 mg or 6 mg of each peptide in 150 μL of sterile, chilled water resulting in two stock solutions for each peptide. Then, 100 μL of each stock was added to a separate glass vial. A 100 μL portion of chilled, fresh BTP buffer (100 mM, pH 7.4) containing 300 mM NaCl and 1.2 mg/mL of the respective FITC-dextran or lactoferrin was added to the stock solution. Samples were carefully agitated to initiate hydrogelation, resulting in 0.5 and 2.0 wt % peptide gels, respectively, of a final total volume of 200 μL containing 0.6 mg/mL FITC-dextran or protein. Hydrogels were made in cylindrical glass vials with only the top surface exposed for release and had approximate heights of 0.35 cm from the bottom of the vial. After 24 hrs, 1 mL of physiological buffer was added to the top of gel. At scheduled time points, the entire volume of buffer above the gel was removed and replaced with fresh buffer. Macromolecule concentration was determined for each removed aliquot as a function of time. Each time point was performed in triplicate and experiments were carried out for 28 days. The concentration of dextran in the stock solutions and in the supernatant was determined by UV-Vis spectroscopy from the area under the absorbance curve between the wavelengths of 415 and 535 nm (FITC has $Abs_{MAX}$ at 492 nm). Calculated areas were converted to concentration values via calibration curves. Release profiles for the protein, lactoferrin, were determined in a similar manner except that protein concentration was assessed by absorbance at 280 nm and compared with a calibration curve.

Properties of the Gels

Modulation of Mesh Size

It was possible to vary the mesh sizes of MAX1 gels simply by adjusting the weight percent of MAX1. Since these gels do not swell appreciably, the increased peptide concentration results in the formation of more fibrils that entangle and crosslink into the network. Thus, higher weight percent gels are more mechanically rigid and have smaller mesh sizes than gels of the same volume prepared with lower concentrations of peptide. For example, FIG. 2(A) shows rheological data monitoring the onset of the storage modulus, a measure of the material's mechanical rigidity, as a function of time for MAX1 gels prepared at different weight percents. Here, gelation is triggered by the addition of a solution of sodium chloride to an aqueous solution of unfolded peptide. It is clear that as the weight percent increases, the resultant storage modulus of the gels increase.

FIG. 2(A) shows time sweep rheological data measuring the storage moduli of 0.5, 1.0, and 2.0 wt % MAX1 hydrogels as a function of time. FIG. 2(B) shows mesh sizes (ξ) of MAX1 hydrogels as a function of peptide weight percent. Inset is a table of MAX1 peptide weight percent, plateau moduli from frequency sweep data, and the respective mesh size. FIG. 2(C) shows time sweep rheological data measuring the storage moduli of 1 wt % MAX1 and HPL8 hydrogels as a function of time. FIG. 2(D) shows mesh sizes (ξ) of HPL8 hydrogels as a function of peptide weight percent. Inset is a table of HPL8 peptide weight percent, plateau moduli from frequency sweep data, and the respective mesh size. Hydrogels were formed in physiological buffer at 25° C. All experiments were performed in triplicate.

Estimation of Mesh Size

Rheology can also be used to estimate the mesh sizes of viscoelastic gels. These peptide hydrogels have been previously shown to display characteristics of semiflexible biopolymers. Therefore the Mackintosh theory can be used to relate the plateau storage modulus of a gel to its mesh size according to Equation 6.

$$G'_p \sim k_B T \frac{l_p^2}{\xi^5} \quad [6]$$

The plateau modulus, $G'_p$, is determined from dynamic frequency sweep data and is defined as the storage modulus at the frequency where the loss modulus is a minimum. $G'_p$ is nearly identical in value to the final storage modulus in FIG. 2(A). In Equation 6, kB is the Boltzmann's constant, T is the temperature at which the hydrogel is formed (25° C.; 298° K), $l_p$ is the persistence length of the fibrils (~55 nm), and ξ is the characteristic mesh size of the network. FIG. 2(B) shows the calculated mesh sizes for MAX1 gels as a function of peptide weight percent. It can be seen from the data that increasing the concentration by a factor of four resulted in about a two-fold decrease in the mesh size; the 0.5 wt % gel had a mesh size of 49 nm as compared with 22 nm for the 2 wt % gel.

The mesh size of the β-hairpin gels can also be modulated by the varying the peptide's sequence. The replacement of a lysine residue of MAX1 at position 15 with glutamic acid results in HPL8. This peptide folds and self-assembles faster than MAX1 under identical solution conditions and peptide weight percent. FIG. 2(C) shows the onset of gelation as a function of time for 1 wt % gels formed by MAX1 and HPL8. Both peptides form moderately rigid viscoelastic gels. However, HPL8 forms a more rigid hydrogel more quickly than MAX1. After 60 minutes, the storage modulus of HPL8 is more than an order of magnitude larger that of the MAX1 hydrogel. Correspondingly, the mesh size of the 1 wt % HPL8 gel (23±0.4 nm) is smaller than the 1 wt % MAX1 gel (34±0.2 nm).

Figure 2:
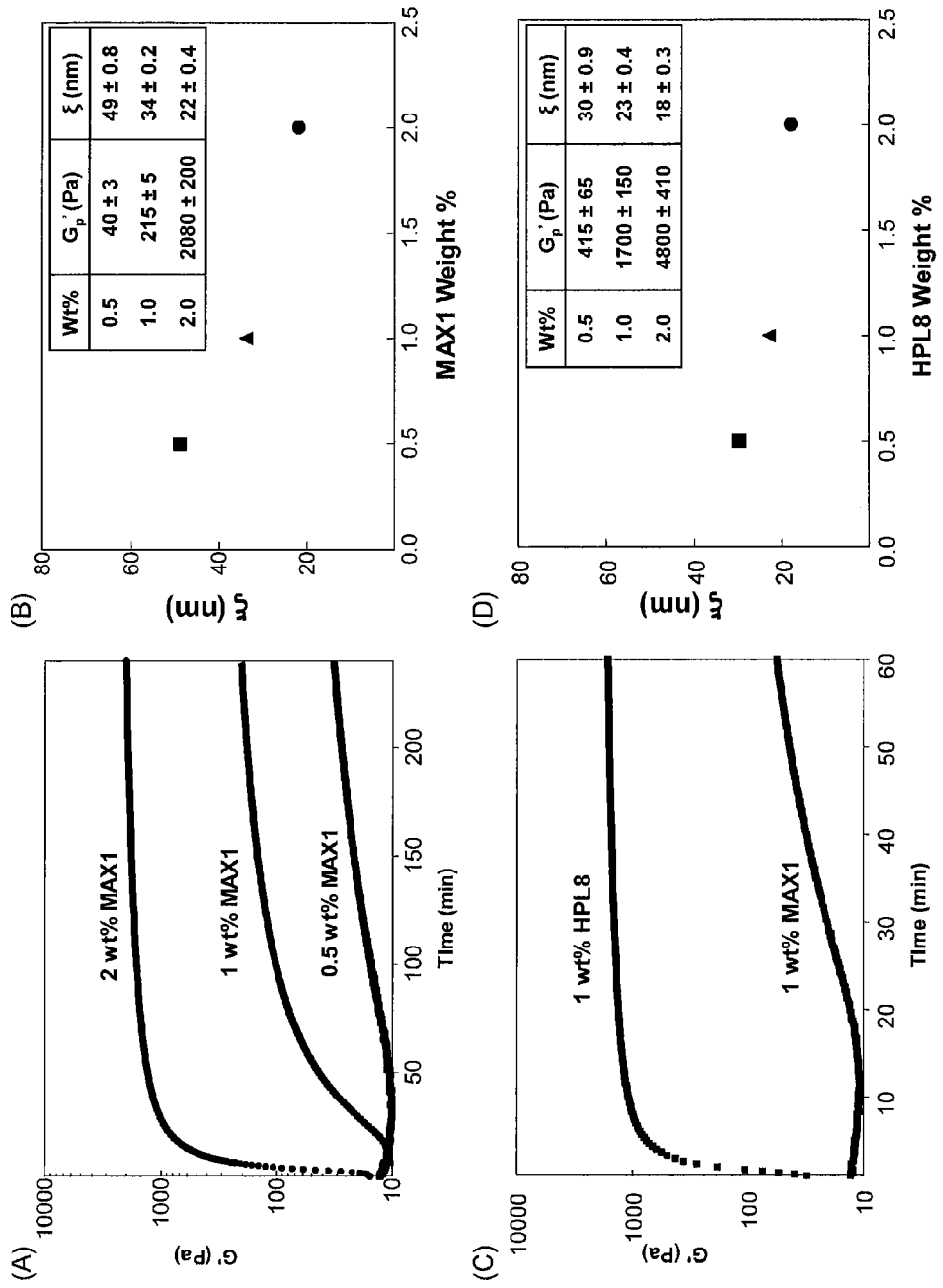
FIG. 2(A) shows time sweep rheological data measuring the storage moduli of 0.5, 1.0, and 2.0 wt % MAX1 hydrogels as a function of time.
FIG. 2(B) shows mesh sizes (ξ) of MAX1 hydrogels as a function of peptide weight percent.
FIG. 2(C) shows time sweep rheological data measuring the storage moduli of 1 wt % MAX1 and HPL8 hydrogels as a function of time.
FIG. 2(D) shows mesh sizes (ξ) of HPL8 hydrogels as a function of peptide weight percent.

Similar to MAX1 gels, the mesh size of HPL8 gels can be varied by adjusting the peptide concentration. FIG. 2(D) shows the mesh sizes of HPL8 gels as a function of peptide weight percent, with mesh sizes varying from 30 to 18 nm. In addition, comparing FIG. 2(B) with 2(D), the mesh sizes of HPL8 are smaller than the mesh sizes of MAX1 at a given peptide weight percent, again indicating that peptide sequence can be used to modulate mesh size. As seen by reviewing FIG. 2, it was possible to prepare hydrogels of varying mesh size by adjusting either the peptide concentration or the peptide sequence, or both.

Diffusion of Macromolecules within Hydrogels

The mesh sizes (18-49 nm) of these gels were on the order of the hydrodynamic diameters of the macromolecules being used in this study (6-12 nm), and the inventors expected that both mesh size and any physical interactions between the macromolecule and the fibrillar network would affect diffusion. Thus, before bulk release studies were performed, the diffusivity of macromolecules within the peptide matrices was first studied to ascertain whether the peptide matrix could interact with incorporated macromolecules. Diffusion coefficients (D) of FITC-labeled dextrans within MAX1 and HPL8 of differing weight percent were determined via FRAP experiments employing laser scanning confocal microscopy. In this experiment, fluorescent macromolecules were homogeneously incorporated within the network and a high intensity laser was used to photobleach them within a defined area of the gel. The recovery of fluorescence after photobleaching, due to neighboring fluorescent macromolecules diffusing into the bleached area, was measured as a function of time. The resultant data were fitted to determine the diffusion coefficient (D) of the macromolecules within the network, using Equations 3 and 4. For example, FIG. 3 shows a typical FRAP experiment for the 70 kD FITC-dextran incorporated into a 2 wt % MAX1 hydrogel.

Figure 3:
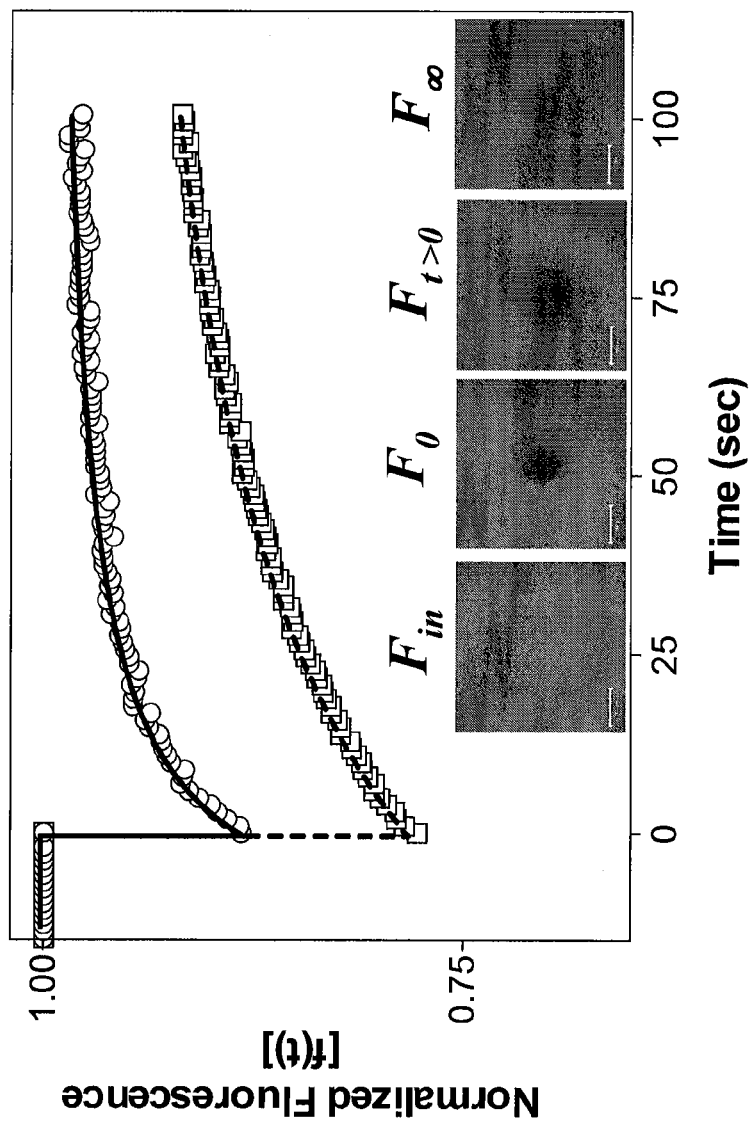
FIG. 3 shows normalized fluorescence recovery (f(t)) of 70 kD FITC-dextran (0.6 mg/mL) in physiological buffer, with (□) and without (○) 2 wt % MAX1. The inset shows confocal microscopy images corresponding to the FRAP experiment for a 2 wt % MAX1 gel.

FIG. 3 shows normalized fluorescence recovery (f(t)) of 70 kD FITC-dextran (0.6 mg/mL) in physiological buffer, with (□) and without (○) 2 wt % MAX1. The inset shows confocal microscopy images corresponding to the FRAP experiment for a 2 wt % MAX1 gel, indicating the corresponding fluorescence recovery in real time of the macromolecule in the gel. $F_{in}$ corresponds to the initial fluorescence before bleaching, $F_0$ is the fluorescence measurement immediately after photobleaching, $F_{t>0}$ corresponds to the recovery of fluorescence after photobleaching and $F_\infty$ corresponds to maximal recovery of fluorescence at the end of the experiment. The scale bar=100 μm.

It can be seen that the fluorescence recovery of the macromolecule in the hydrogel was slower than in the buffer solution, indicating that the mobility of the macromolecule within the gel was more restricted than in buffer.

The self-diffusion coefficients (D) for FITC-dextrans within MAX1 and HPL8 gels prepared at 25° C. are summarized in Table 1, where "probe" refers to FITC-dextran.

TABLE 1

| Probe MW (kD) | Probe Diameter $d_H$ (nm) | MAX1 Diffusion Coefficient, D ($10^{-8}$ cm²/sec) | | | MAX8 Diffusion Coefficient, D ($10^{-8}$ cm²/sec) | | |
|---|---|---|---|---|---|---|---|
| | | 0.5 wt % | 1.0 wt % | 2.0 wt % | 0.5 wt % | 1.0 wt % | 2.0 wt % |
| 20 | 6.2 | 43.4 ± 5.3 | 34.5 ± 5.8 | 25.9 ± 4.1 | 41.0 ± 5.8 | 31.8 ± 5.1 | 19.2 ± 2.6 |
| 70 | 9.3 | 30.0 ± 4.0 | 22.2 ± 4.5 | 15.5 ± 3.0 | 23.3 ± 5.6 | 18.9 ± 3.9 | 11.3 ± 3.5 |
| 150 | 12.1 | 10.1 ± 2.0 | 8.2 ± 1.3 | 4.6 ± 1.3 | 7.3 ± 2.1 | 5.4 ± 1.8 | 4.0 ± 0.9 |

Comparing the diffusion coefficients of each of the macromolecules in 0.5 wt % and 2.0 wt % (the two weight percent extremes), macromolecular mobility was restricted by a factor of 2 in both MAX1 and HPL8 gels.

Figure 4:
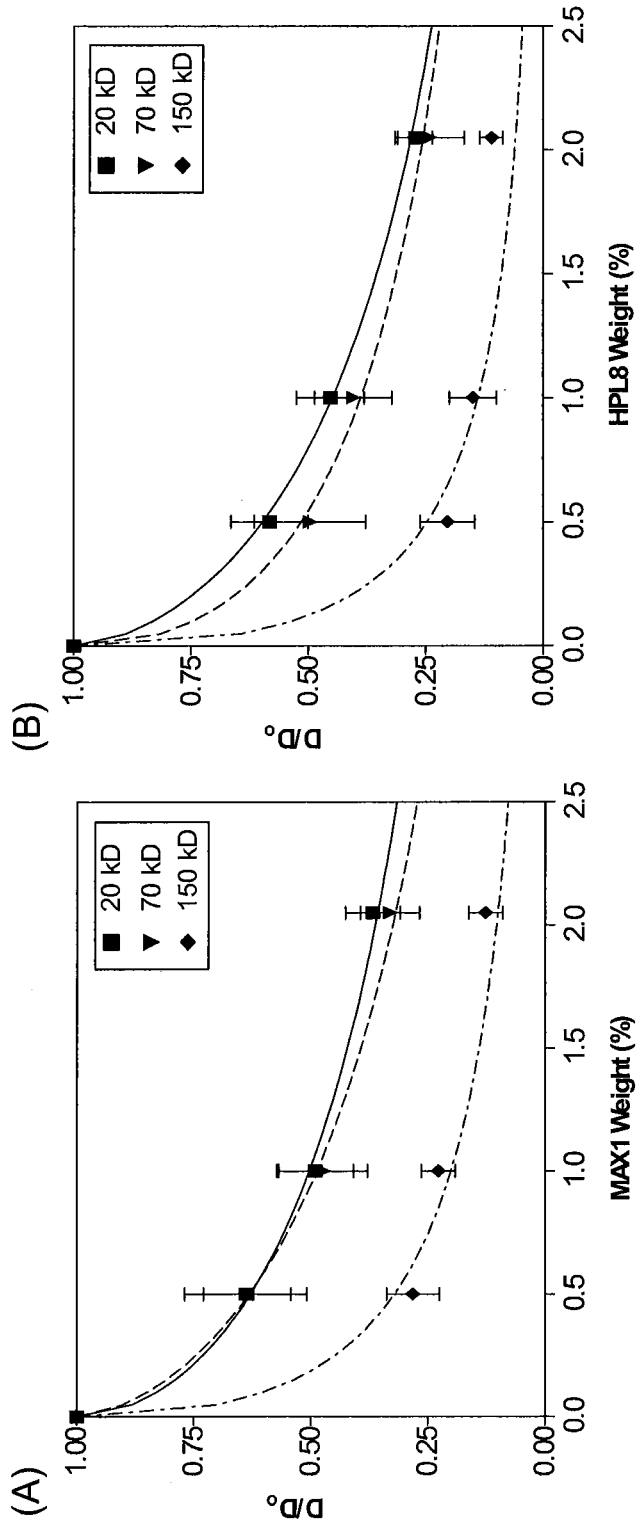
FIG. 4(A) shows diffusion coefficients of macromolecules in MAX1 hydrogels, normalized with respect to the diffusion coefficients of the macromolecules in buffer alone.
FIG. 4(B) shows diffusion coefficients of macromolecules in HPL8 hydrogels, normalized with respect to the diffusion coefficients of the macromolecules in buffer alone.

FIG. 4 shows the data of Table 1, normalized with respect to the diffusion coefficients of the macromolecules in buffer alone ($D_o$) and plotted as a function of peptide weight percent.

FIG. 4(A) shows the results for MAX1 gels. Interestingly, when macromolecules were incorporated in the most dilute gel, 0.5 wt %, the gel network was capable of strongly influencing macromolecular mobility. For example, the 20 kD macromolecule diffusion was only 60% of what was observed in buffer solution alone; the mobility of the largest macromolecule, 150 kD, was reduced to 25%. With increasing gel weight percent, the mobility of all the macromolecules became further restricted as mesh size decreased due to higher weight percents of MAX1. Also evident is that at a particular gel weight percent, the largest macromolecule, 150 kD ($d_H$=12.1 nm) diffused at a slower relative rate than those of smaller hydrodynamic diameters, and there was little discrimination between the two smaller macromolecules at all weight percents. This indicates that as the macromolecule hydrodynamic diameter approached the mesh size, macromolecular mobility was significantly hindered. FIG. 4(B) shows the results for HPL8 hydrogels, and the trends were similar.

It was tempting to interpret the trends seen in FIGS. 4(A) and 4(B) based on mesh size alone. However, because the sizes of the macromolecules approached the mesh size of the gels used in this study, it was likely that interactions between the macromolecules and the network also influence macromolecular mobility. Macromolecule-matrix interactions can be investigated by comparing the diffusion coefficients of a distinct macromolecule incorporated into networks formed from two different peptide sequences. For example, 0.5 wt % MAX1 hydrogels have a mesh size that was about 60% larger than 0.5 wt % HPL8 (49 nm versus 30 nm). One would expect that the diffusion coefficient of a given macromolecule in the 0.5 wt % MAX1 gel would be significantly larger than in the HPL8 gel if mesh size alone dictated macromolecular diffusion. However, the diffusion coefficients of any given macromolecule within the two peptide networks were the same within error. This suggested that some kind of macromolecule-matrix interactions were also affecting macromolecular mobility.

Previous small angle neutron scattering (SANS) and microscopy studies of the gels revealed that the local fibrillar morphology of MAX1 and HPL8 networks are similar. Both peptides form fibrils of homogeneous diameter (~3 nm) with similar persistence lengths. Also, on the molecular level, CD and FTIR spectroscopy reveals that both peptides adopt well-defined β-hairpins indicating that the secondary structure of peptides assembled into fibrils are similar. The most apparent difference between the two peptide gels lies in the composition of amino acids that comprise each of the peptides. MAX1 contains 8 positively charged lysine side chains and an N-terminal ammonium group giving it an overall charge of about +9 at neutral pH. HPL8 consists of a sequence in which one of the lysines is replaced by a glutamic acid, giving it an overall charge of about +7, as well as a negatively charged carboxylate side chain displayed from each peptide assembled along a given fibril. Therefore, at similar peptide weight percents, MAX1 hydrogels are more electropositive than HPL8 gels. In addition, the fibrils that constitute HPL8 gels contain point negative charges distributed along their long axes. The dextrans used in this work were labeled with fluorescein isothiocyanate (FITC), which contains a free carboxylate with a $pK_a$ of 6.5, and therefore, is anionic at neutral pH. The concentration of fluorescein (37 μM), regardless of which dextran is used, was constant in these studies. In the FRAP experiments, diffusion was more hindered in MAX1 gels than in HPL8 gels. Therefore, this suggests that the negatively charged FITC-dextrans interacted more strongly with the more electropositive MAX1 gels than with HPL8 gels. In addition to the differences between the overall charge state of the two peptides (MAX1: ~+9, HPL8: ~+7), the negatively charged glutamic acid side chain of HPL8 could further repel the negatively charged FITC labels from interacting with the peptide fibrillar network. Thus, without wishing to be bound by any particular theory or explanation, the inventors believe that anionic macromolecules diffuse more slowly within MAX gels than do cationic or neutral macromolecules due to charge interactions with the gels. If this is indeed the reason, it is unexpected because it has been thought that the positive charge on the strands that constitute MAX peptide hydrogels is extensively screened by the presence of NaCl, which has been considered necessary for gel formation.

Bulk Release Studies

The bulk release of the same dextrans used in the FRAP studies was assessed from gels that were formed in the presence of the macromolecule, a method that allows precise control of macromolecule concentration. For example, a 2 wt % gel that encapsulates 0.6 mg/mL of a particular macromolecule can be prepared by first dissolving the peptide in aqueous solution and adding this to a solution of macromolecule in pH 7.4 buffer containing salt. The 1:1 addition of these two solutions initiates hydrogelation and results in the homogeneous incorporation of the macromolecule.

Equivalent values of plateau moduli are realized for gels of equivalent weight percent that encapsulate macromolecules compared with gels containing no macromolecules. Thus, encapsulation of macromolecules has not been found to affect the rheological properties of the hydrogels.

The 20, 70, and 150 kD macromolecules were encapsulated into 0.5 and 2.0 wt % MAX1 and HPL8 gels. Gels were allowed to cure for 24 hours after which 1 mL of buffer was added to the top of the gel. FIGS. 5(A) and 5(B) show the amount of labeled dextran released from the gels ($M_t$) divided by the initial encapsulated mass ($M_0$) over a 28-day period. At each allotted time point, the buffer was removed from the top of the gel, the released macromolecule was quantified by UV-Vis absorbance, and fresh buffer was added for the next time point. It should be noted that upon the addition of buffer to the top of the gels, the volume of gel remained constant and no swelling was observed. Also, during the release studies, there was no detectable change in hydrogel height and no evidence of surface erosion or degradation. Therefore, the release of dextrans encapsulated in these nondegradable hydrogels was controlled solely by diffusion and any possible interactions between the macromolecule and the peptide network.

Figure 5:
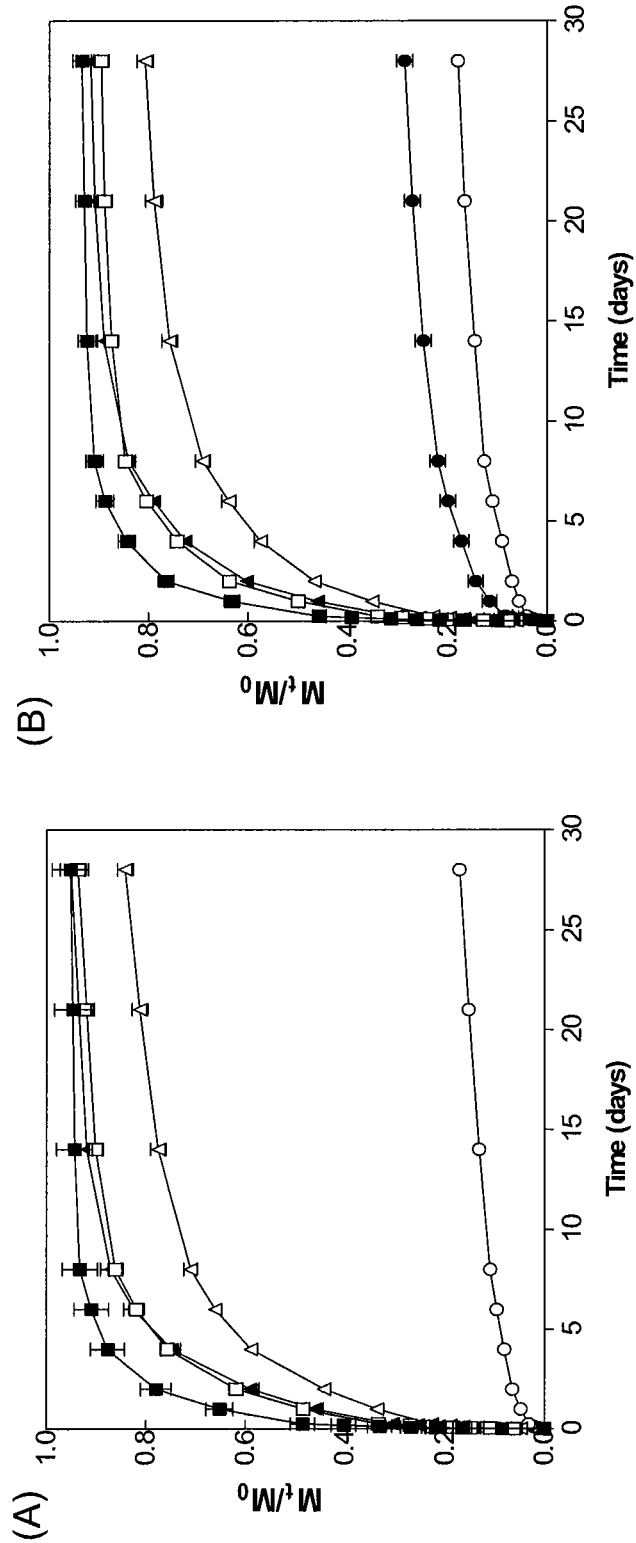
FIG. 5(A) shows cumulative bulk release plots of 20 kD, 70 kD, and 150 kD FITC-dextrans from 0.5 wt % and 2.0 wt % MAX1 hydrogels.
FIG. 5(B) shows cumulative bulk release plots of 20 kD, 70 kD, and 150 kD FITC-dextrans from 0.5 wt % and 2.0 wt % HPL8 hydrogels.

FIG. 5 shows cumulative bulk release of 20 kD (■), 70 kD (▲), and 150 kD (●) FITC-dextrans from 0.5 wt % (closed symbols) and 2.0 wt % (open symbols) from (A) MAX1 and (B) HPL8 hydrogels. Hydrogels were formed in physiological buffer at 25° C. Release studies were collected at 25° C.

FIG. 5(A) shows that for the 0.5 wt % MAX1 gel, the fastest release was obtained for the smallest macromolecule (20 kD, $d_H$=6.2 nm). This was expected since this gel had the largest mesh size of those studied. The 20 kD macromolecule and the 70 kD macromolecule were released with nearly identical rates from 2.0 wt % and 0.5 wt % MAX1 gels, respectively. This is consistent with the FRAP analysis which shows that these two macromolecules have similar diffusion coefficients when incorporated into the respective gels (Table 1: $D_{20kD-2wt\%MAX1}$ = 25.9±4.1, $D_{70kD-0.5wt\%MAX1}$ = 30.0±4.0). It is also seen that the 70 kD macromolecule was released more slowly from a 2 wt % gel than from a 0.5 wt % gel. After 28 days, only 80% was released. The 150 kD FITC-dextran, which is the largest macromolecule in the study and similar in size to many therapeutic antibodies, showed the slowest release from the 2 wt % gel. Data are shown only for the 2 wt % gel because solutions of 0.5 wt % MAX1 with 150 kD FITC-dextran did not form hydrogels. (The highly negatively charged dextran prevents low concentrations of MAX1 from self-assembling. However, neutral, unlabeled 150 kD dextran can be encapsulated into 0.5 wt % MAX1 gels.)

FIG. 5(B) shows similar trends for the release of macromolecules from the HPL8 gels, but with a notable difference that it was possible to encapsulate the 150 kD macromolecule in 0.5 wt % HPL8 gels. Nearly 70% of this large macromolecule was retained within the matrix even after 28 days.

The characteristic time for release of 50% of the initial mass ($t_{50\% \, released}$) is given in Table 2 for the 20 and 70 kD macromolecules. Since less than 50% of the 150 kD was released over the time course of the study, the $t_{25\% \, released}$ value for this macromolecule is reported for both the MAX1 and HPL8 gels. The $t_{50\% \, released}$ values ranged from about 8, 11, 24, and 28 hrs for the smallest 20 kD macromolecule depending on peptide sequence and gel weight percent. The $t_{50\% \, released}$ values for the 70 kD macromolecule ranged from about 31 to 67 hrs. The $t_{25\% \, released}$ values for the largest 150 kD macromolecule ranged from 14 to greater than 28 days.

TABLE 2

| Peptide | $t_{50\% \, released}$ (hrs) | | $t_{25\% \, released}$ (days) |
| --- | --- | --- | --- |
| | 20 kD FITC-dextran | 70 kD FITC-dextran | 150 kD FITC-dextran |
| 0.5 wt % Max1 | 8 ± 3 hrs | 32 ± 3 hrs | — |
| 2.0 wt % Max1 | 28 ± 3 hrs | 67 ± 4 hrs | >28 days |
| 0.5 wt % Max8 | 11 ± 1 hrs | 31 ± 2 hrs | 14 ± 3 days |
| 2.0 wt % Max8 | 24 ± 2 hrs | 63 ± 5 hrs | >28 days |

The characteristic release times in Table 2 are consistent with the FRAP-derived diffusion coefficients in Table 1. Table 2 shows that for any given dextran, the release rate was nearly twice as fast from the 0.5 wt % gel as compared to the 2 wt % gel. Table 1 shows the same trend in diffusion coefficients. This demonstrates that the release rates scale with the diffusion coefficients determined from FRAP.

The FRAP data from the dextrans suggests that electrostatics could influence the bulk release of a given macromolecule from the gel network. This possibility was further investigated by measuring the bulk release of two differently charged macromolecules that have similar molecular weights and hydrodynamic diameters from 2 wt % MAX1 gels.

Figure 6:
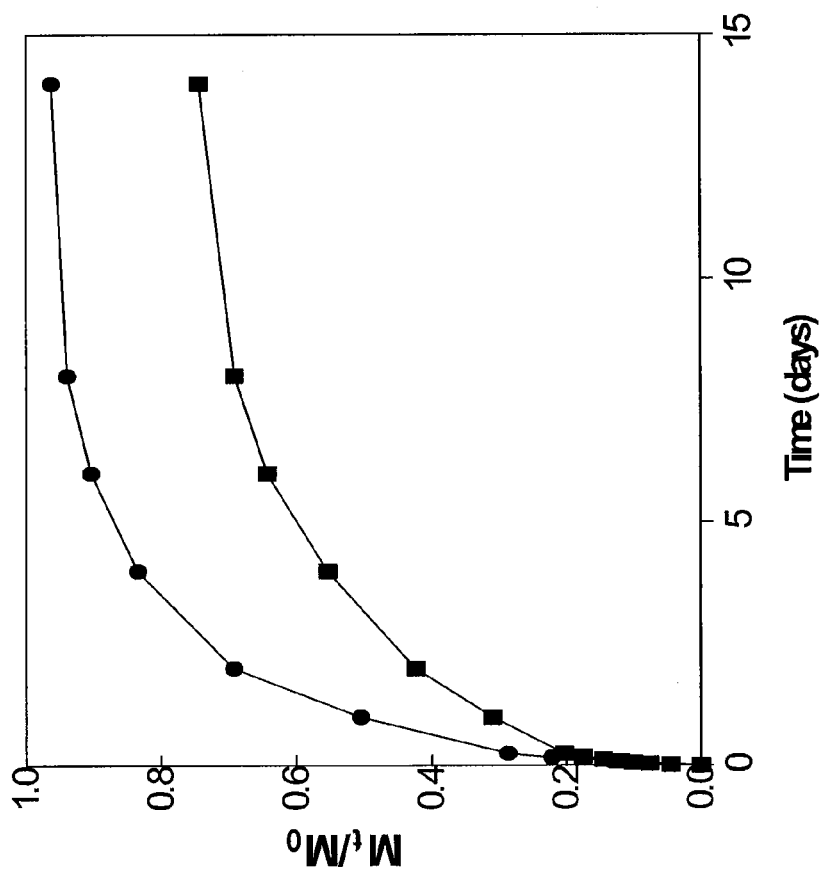
FIG. 6 shows cumulative bulk release plots of 70 kD FITC-dextran (■) and lactoferrin (●) from 2.0 wt % MAX1 hydrogels.

FIG. 6 shows cumulative bulk release plots of the negatively-charged 70 kD FITC-dextran (■) (pI~6.5) and the positively-charged lactoferrin (●), of similar weight (77 kD, pI~8.4-9.0), at pH 7.4 and 25° C. The hydrodynamic diameters of the dextran and protein are similar, 9.3 nm and 7.2 nm, respectively, but their charge state varies considerably. The inventors used 2 wt % MAX1 gels since these gels have small mesh sizes, the peptide networks are highly positively charged and, thus, electrostatic effects should be pronounced if present. The data show that the positively charged protein was released more quickly than the negatively charged dextran. After 2 days, ~70% of the lactoferrin was released compared to ~40% of the FITC-dextran. These results suggest that the charge state of the macromolecule affects the release from the peptide hydrogel, with anionic macromolecules releasing more slowly.

MAX Gels Containing Anionic, Neutral and Cationic Proteins

The macromolecules in the foregoing study varied not only by charge, but also by overall molecular structure and functionality. FITC-dextran is a polysaccharide and lactoferrin is a protein. Therefore, to clarify whether charge was indeed affecting release of the macromolecules from MAX gels, further experiments were performed using only proteins: α-lactalbumin (bovine milk, Type I), lysozyme (chicken egg white), albumin (bovine serum), lactoferrin (bovine milk), and IgG (human serum), all purchased from Sigma-Aldrich. Techniques were similar to those described above, and are detailed here as necessary to indicate differences.

Materials and Methods

Dynamic Oscillatory Rheology

Oscillatory rheology experiments were performed on a Paar Physica MCR 500 rheometer using 25 mm diameter stainless steel parallel plate geometry. Hydrogels were prepared directly on the rheometer plate in the following manner. HPL8 peptide stock solutions were first prepared in glass vials by dissolving 4 mg of peptide in 200 μL of sterile, chilled water. To this solution, 200 μL of chilled BTP buffer (100 mM, pH 7.4) containing 300 mM NaCl was added. To prepare gels that directly encapsulate the proteins, 200 μL of chilled BTP buffer (100 mM, pH 7.4) containing 300 mM NaCl and 2 mg/mL of the respective protein was added to the peptide solution, resulting in a 1.0 wt % gel at a final total volume of 400 μL. Then, 300 μL of the resulting solution was quickly added to the rheometer plate, which was pre-equilibrated at 5° C. The parallel plate tool was then lowered to a gap height of 0.5 mm and the temperature was ramped linearly to 37° C. to initiate gelation.

For gels formed and then tested without pre-shearing (referred to as the "in situ" gelation experiment), a dynamic time sweep was performed to measure the storage (G') and loss (G") modulus at a frequency of 6 rad/sec and 0.2% strain as a function of time for 1 hour. A dynamic frequency sweep (0.1 to 100 rad/sec at constant 0.2% strain) was then performed, followed by a dynamic strain sweep (0.1 to 1000% strain at constant 6 rad/sec), which was used to verify that the former measurements were within the linear viscoelastic regime.

For the shear-thinning and recovery experiment, a dynamic time sweep was performed at a frequency of 6 rad/sec and 0.2% strain for 1 hour. This was immediately followed by a 30 second period, in which 1000% strain at a frequency of 6 rad/sec was applied to the sample. This was then followed by another one hour dynamic time sweep (6 rad/sec, 0.2% strain) to measure the sample's moduli recovery after shear. A dynamic frequency sweep (0.1 to 100 rad/sec at constant 0.2% strain) and a dynamic strain sweep (0.1 to 1000% strain at constant 6 rad/sec) were also performed for these rheology experiments.

Bulk Release Studies

For the bulk release studies, HPL8 peptide stock solutions were first prepared in glass vials by dissolving 4 mg of each peptide in 200 μL of sterile, chilled water. Then, 150 μL of each stock was added to a separate glass vial. 150 μL of chilled, fresh BTP buffer (100 mM, pH 7.4) containing 300 mM NaCl and 2 mg/mL of the respective protein was added to the stock solution. Samples were carefully shaken to initiate hydrogelation, resulting in 1.0 wt % gels of a final total volume of 300 μL containing 1 mg/mL protein. Samples were placed in an incubator at 37° C. for 3 hours. To mimic syringe delivery, after buffer was added to the peptide aqueous solution, the resultant solution was drawn into a 1 mL syringe and allowed to gel directly in the syringe for 1½ hours in an incubator at 37° C. The sample was then sheared through a 26 3/8 gauge needle into a separate glass vial. The sample was then placed in the incubator at 37° C. for another 1½ hours prior to the release experiment.

To measure bulk release of the anionic macromolecule, hydrogels were extracted with physiological buffer over a 28-day period, according to the following general protocol, referred to herein as "28-day extraction."

A 300 μL sample of hydrogel was made in a cylindrical glass vial having a diameter of 10 mm, with only the top surface of the gel exposed for release. The gel had an approximate height of 0.5 cm from the bottom of the vial. After 3 hrs, 1 mL of physiological buffer was added to the top of the gel. At scheduled time points of 1 hr, 2 hr, 3 hr, 4.5 hr, 6 hr, 1 day, 2 days, 4 days, 6 days, 8 days, 14 days, 21 days, and 28 days, the entire volume of buffer above the gel was removed and replaced with fresh buffer. Macromolecule concentration was determined for each removed aliquot as a function of time. Each time point was performed in triplicate and experiments were carried out for 28 days. The concentration of protein in the stock solution and in the supernatant was determined from the absorbance at 280 nm by UV-Vis spectroscopy, which was compared to a calibration curve.

Bulk release profiles resulting from 28-day extractions were fit to a 1D nonsteady-state Fickian diffusion model for a macromolecule with a constant diffusion coefficient, D, diffusing through a thin slab with a height, h, where $M_t$ is the mass of protein released at time t and $M_{eq}$ is the mass of protein released at the end of one 28 days. The 95% confidence intervals of the fitted diffusion coefficients were also calculated.

$$\frac{M_t}{M_{eq}} = 1 - \sum_{n=1}^{\infty} \frac{8}{(2n+1)^2 \pi^2} \exp\left(-\frac{(2n+1)^2 \pi^2 Dt}{h^2}\right) \quad [1]$$

tein in the stock solutions and in the supernatants was determined from the absorbance at 280 nm by UV-Vis spectroscopy.

Properties of the Gels

Figure 7:
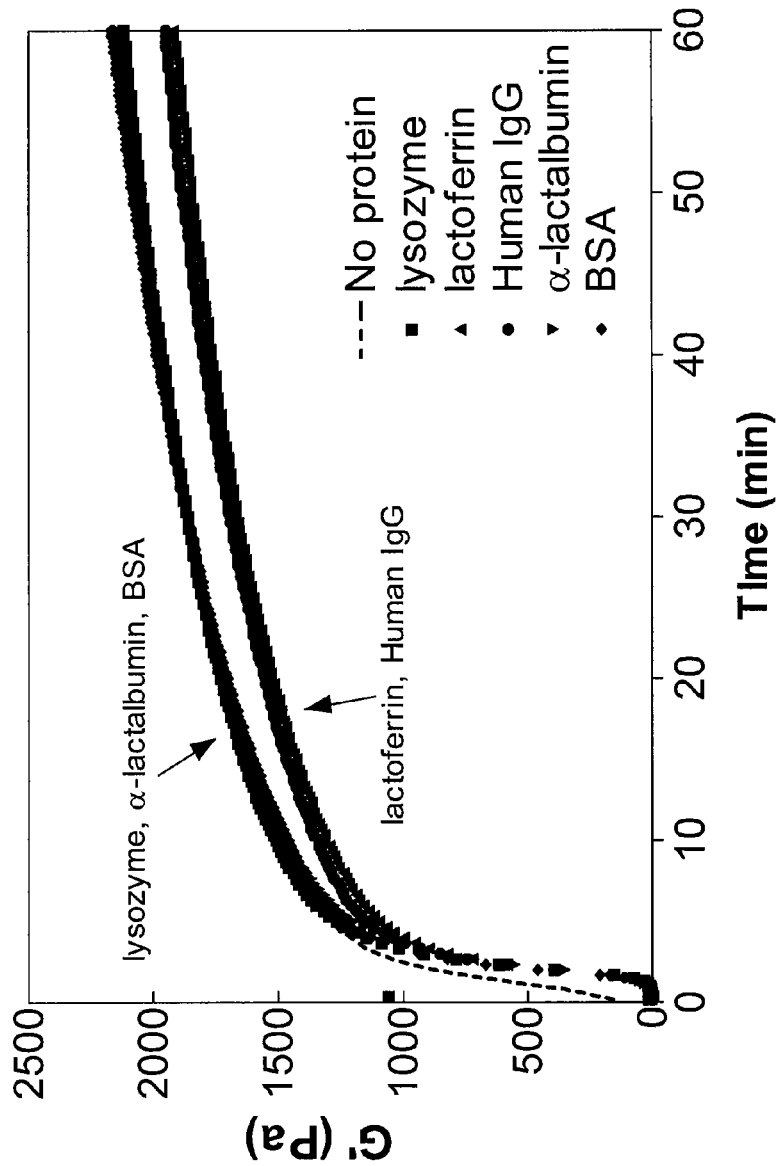
FIG. 7 shows dynamic oscillatory time sweeps of 1 wt % HPL8 hydrogels in physiological buffer at 37° C. in the presence of the following model proteins: lysozyme, lactoferrin, Human IgG, α-lactalbumin and bovine serum albumin (BSA).

FIG. 7 shows dynamic oscillatory time sweeps of 1 wt % HPL8 hydrogels in physiological buffer at 37° C. in the presence of the following model proteins: lysozyme, lactoferrin, Human IgG, α-lactalbumin and bovine serum albumin (BSA). Dashed line represents dynamic time sweep of peptide hydrogel alone. The storage modulus (G'), a measure of the material's mechanical rigidity, is shown as a function of time. At the end of a one-hour experiment performed as described above under Dynamic Oscillatory Rheology for gels formed and then tested without pre-shearing, a 1 wt % HPL8 gel had a storage modulus of 2200±250 Pa. The mesh sizes of HPL8 hydrogels have been previously approximated using the Mackintosh theory for semiflexible, crosslinked polymer networks. Applying the same model for this system indicates a hydrogel with a mesh size of 22-23 nm. This is on the order of the hydrodynamic diameters of the proteins used in this study, and therefore should impart physical interactions influencing macromolecular diffusion.

Proteins of varying size and charge (Table 3) were incorporated in the high salt buffered solution and then added to the aqueous HPL8 solution to trigger self-assembly. It is clear from FIG. 7 that the resultant hydrogels encapsulating the proteins had similar hydrogelation kinetics and yielded materials with equivalent storage modulus (~2000 Pa). Visual assessment of the materials confirmed that the materials were rigid, self-supporting gels (not shown).

The hydrodynamic diameters of the studied proteins, as well as other properties, are shown in Table 3. Depending on the protein's isoelectric point (pI) and the pH of the solution, the protein molecules had a net positive (pI>pH), a net negative (pI<pH), or neutral (pI~pH) charge exposed on its surface.

TABLE 3

| Protein | Molecular Weight (kD) | Hydrodynamic diameter (nm) | $D_{aq}$(37° C.) ($\times 10^{-8}$ cm$^2$/sec) | Isoelectric point, pI | Charge at pH 7.4 |
| --- | --- | --- | --- | --- | --- |
| α-lactalbumin | 14.1 | 3.2 | 142 | 4.2-4.5 | − |
| Lysozyme | 14.7 | 4.1 | 111 | 11.0 | + |
| Bovine Serum Albumin (BSA) | 66 | 7.2 | 63 | 4.6-4.8 | − |
| Lactoferrin | 77 | 6.1 | 74 | 8.4-9.0 | + |
| Human Immunoglobulin G (IgG) | 146 | 10.7 | 41 | 5.8-8 | ∅ |

Adsorption Studies

For the bulk adsorption studies, HPL8 peptide stock solutions were first prepared in glass vials by dissolving 4 mg of each peptide in 200 μL of sterile, chilled water. Then, 150 μL of each stock was added to a separate glass vial. 150 μL of chilled, fresh BTP buffer (100 mM, pH 7.4) containing 300 mM NaCl was added to the stock solution. Samples were carefully shaken to initiate hydrogelation, resulting in 1.0 wt % gels of a final total volume of 300 μL. Samples were placed in an incubator at 37° C. for 3 hours. After 3 hrs, 300 μL of physiological buffer containing 1 mg/mL of the respective protein was added to the top of the gel. The hydrogels were then placed in the incubator at 37° C. After 48 hours, the entire volume of buffer above the gel was removed and replaced with 1 mL of fresh buffer. This buffer wash was repeated after 48 hours twice more for a total of three washes. The experiment was performed in triplicate. The concentration of pro- Bulk Protein Release from Peptide Hydrogels The bulk release profiles of the encapsulated proteins from the 1 wt % HPL8 gels were monitored for a 28-day period.

Figure 8:
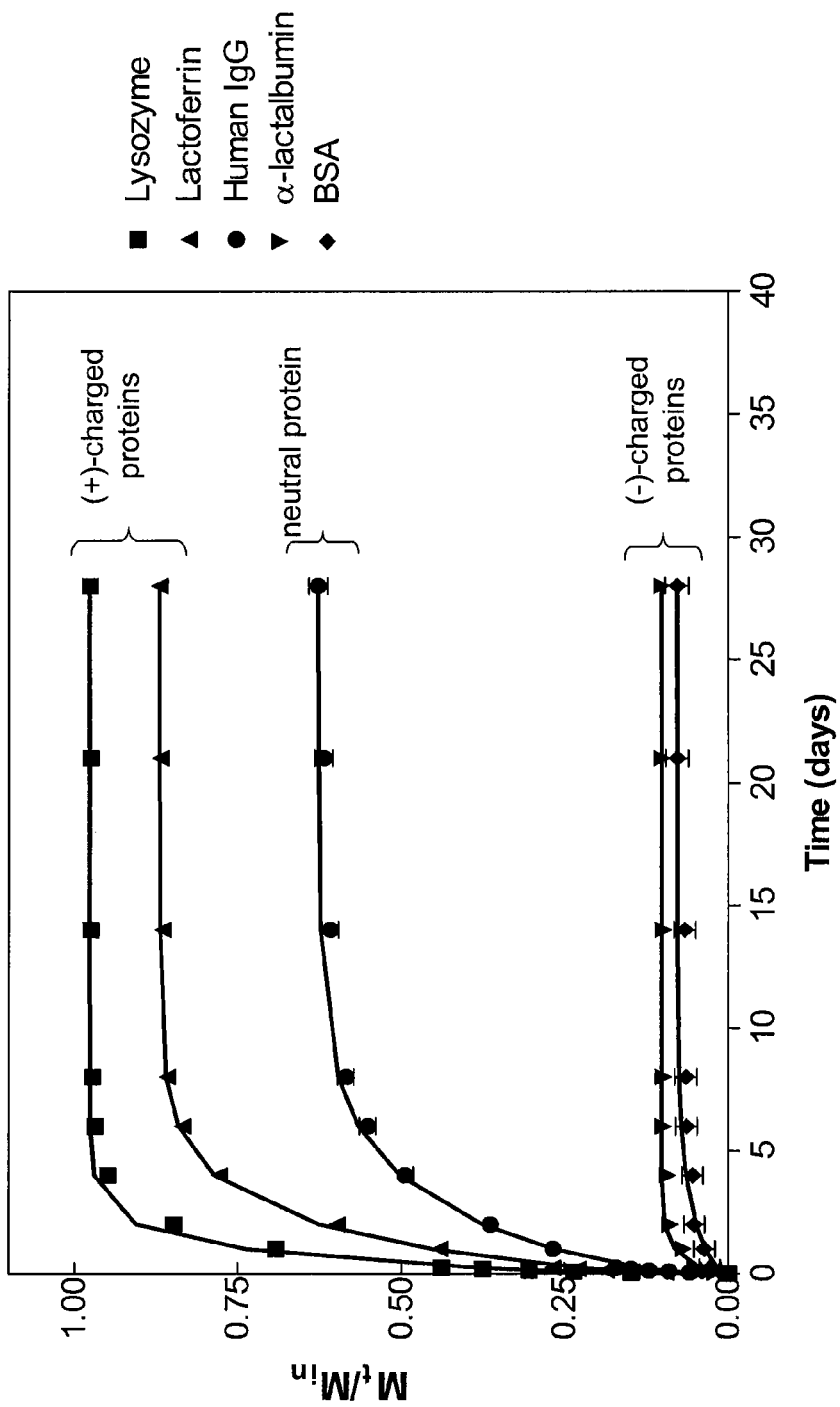
FIG. 8 shows cumulative release profiles ($M_t/M_{in}$) of proteins from 1 wt % HPL8 hydrogels over a 28-day period.

FIG. 8 shows cumulative release profiles ($M_t/M_{in}$) of proteins from 1 wt % HPL8 hydrogels in physiological buffer at 37° C. over a 28-day period. The profiles show the amount of protein released from the gels ($M_t$) normalized to the initial protein loading ($M_{in}$). The lines represent diffusion coefficient fits with Equation 1.

No hydrogel swelling or degradation was observed during the experiment, indicating that protein release was primarily controlled by diffusion and any possible interactions between the macromolecules and the peptide network. Circular dichroism measurements of the released protein supernatant at the 24 hour time point confirmed that the proteins retained their native secondary conformation when released, suggesting that the encapsulation process did not irreversibly affect the proteins' structure.

FIG. 8 shows that the positively charged proteins and neutral antibody were gradually released from the positively charged peptide hydrogel with little retention. The fastest release was observed for lysozyme, a small (14 kD, $d_H$=4.1 nm) protein with a net positive charge at pH 7.4. At the end of 28 days, nearly 100% of the protein was released from the peptide hydrogel network. Lactoferrin, a medium-sized, positively charged protein ($d_H$=6.1 nm), was released more slowly, with 85% released after 28 days. The largest protein in the study with an average $d_H$ of 10.7 nm was human IgG, which exhibited the most hindered diffusion with 40% of the antibody still retained in the gel at the end of the experiment. The apparent diffusion coefficients of the protein release are given in Table 4, calculated using a 1D unsteady-state Fickian diffusion model (Equation 1).

Table 4 shows diffusion coefficients ($10^{-8}$ cm$^2$/sec) of model proteins release from 1 wt % HPL8 hydrogels in physiological buffer at 37° C., as determined by Equation 1. $D_{gel}/D_{aq}$ is the ratio of the diffusion coefficients of the proteins in the gel to their corresponding diffusion coefficients in water at 37° C. The Unreleased Amounts indicate percent of protein remaining in hydrogels after 28 days release time, and the Adsorbed Amounts indicate the percent of protein still adsorbed onto hydrogels after three washes.

TABLE 4

| Protein | Diffusion Coefficient ($10^{-8}$ cm$^2$/sec) | $D_{gel}/D_{aq}$ | Unreleased Amount (%) | Adsorbed Amount (%) |
|---|---|---|---|---|
| Lysozyme | 35 ± 6 | 0.32 | 3 ± 1 | 0 ± 6 |
| Lactoferrin | 16 ± 2 | 0.22 | 14 ± 0 | 6 ± 2 |
| Human IgG | 10 ± 1 | 0.24 | 41 ± 1 | 30 ± 3 |
| α-lactalbumin | 41 ± 15 | 0.29 | 91 ± 0 | 84 ± 3 |
| BSA | 11 ± 9 | 0.17 | 94 ± 0 | 80 ± 2 |

It is apparent that the largest protein (Human IgG) had the smallest diffusion coefficient, indicating that as the protein's hydrodynamic diameter approaches the mesh size of the gel, the mobility of the macromolecule becomes more restricted. When compared with the diffusion coefficients of the proteins in an aqueous solution (Table 3), the diffusivities of the proteins in a 1 wt % HPL8 hydrogel were reduced to 20-30% of the value (Table 4), making evident the strong influence of the hydrogel on protein mobility.

α-Lactalbumin ($d_H$=3.2 nm) and BSA ($d_H$=7.2 nm) have similar hydrodynamic diameters as lysozyme and lactoferrin, respectively, but display a net negative surface charge at pH 7.4 (Table 3). The release of these proteins however was greatly impeded by the positive charge of peptide fibrillar network. At the end of 28 days, only 10% of these proteins have been released with the remaining amount retained within the gel. The apparent diffusion coefficients of these proteins were also calculated using Equation 1 and listed in Table 4. Surprisingly, the calculated values of α-lactalbumin and BSA were equivalent within error to the diffusion coefficients that were calculated for their positively charged protein counterparts. Thus, this confirms that although the rate of release for the proteins was dependent on the protein size, the amount of protein retained in the gel after 28 days was largely governed by the electrostatic interactions between the proteins and the peptide network.

Binding Affinity of Proteins to Hydrogel

The strength of the electrostatic interactions between the proteins and the peptide hydrogels was further assessed by surface adsorption studies. Gels of 1 wt % HPL8 in physiological buffer at 37° C. were allowed to cure for three hours, after which an aliquot of a 1 mg/mL protein solution was added to the top of the gel. After 48 hours, the aliquot was removed and the amount of protein in the supernatant was quantified to determine the amount of protein that partitioned into the gel.

Figure 9:
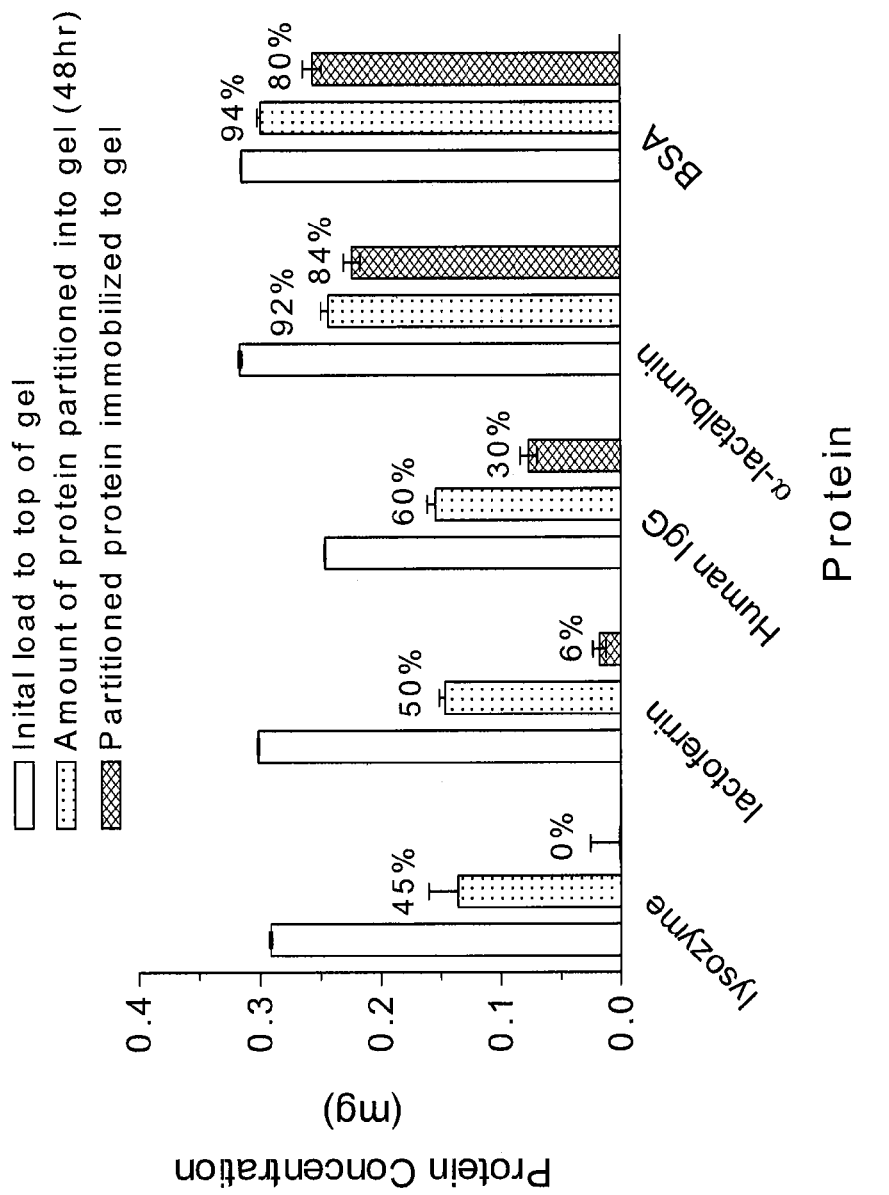
FIG. 9 shows plots indicating initial protein concentration added to the top of 1 wt % HPL8 gels, protein concentration that partitioned into gel after 48 hr incubation with protein solution, and remaining adsorbed protein concentration after three washes over a week period.

FIG. 9 shows plots indicating initial protein concentration added to the top of 1 wt % HPL8 gels, protein concentration that partitioned into gel after 48 hr incubation with protein solution, and remaining adsorbed protein concentration after three washes over a week period. Reported percentages indicate protein concentrations relative to the initial protein load added to the top of the gel.

All proteins, independent of size or charge, partitioned into the hydrogel network to some degree. But of the positively charged proteins (lysozyme and lactoferrin), only 50% of the amount originally present in the stock solution diffused into the 1 wt % HPL8 hydrogels. The large antibody, which had a hydrodynamic diameter approaching the mesh size of the gel, diffused into the gel after 2 days with only 40% remaining in the supernatant. By far the greatest uptake into the gel was observed for the negatively charged proteins, α-lactalbumin and BSA, for each of which more than 90% was sequestered in the gel.

To determine the effective permanence of these interactions, the gels were then successively washed over a week period to remove any non-adsorbed protein from the gel network. After the washes, most of the positively charged proteins were found to have diffused out from the network, with less than 6% of lysozyme and lactoferrin remaining in the peptide hydrogel. Thus, the amount of protein that partitioned into the gel was solely due to diffusion, not to some specific interaction with the components of the gel matrix. Approximately half of the amount of antibody that had partitioned into the gel was still sequestered in the hydrogel. In distinct contrast, the majority of each of the negatively charged proteins was irreversibly adsorbed to the peptide hydrogel, with 80% of the initial load still associated with the network after the multiple washes.

Notably, if one compares the amount of protein that was adsorbed to the hydrogel in the adsorption studies with the amount that was not released in the bulk release experiments (Table 4), the values are equivalent. Thus, the inventors have found that the charge state of the macromolecules greatly affects their interactions with the peptide network, independent of how the protein was encapsulated. Also, this similarity between the two experiments indicates that the protein that remained in the hydrogel in the release experiments was mostly likely adsorbed to the fibrils as opposed to being physically trapped in the network. Only anionic macromolecules appear to be capable of adsorbing, because the effect was not seen with neutral or cationic macromolecules regardless of their size and regardless of the amount and type of MAX peptide used to form the hydrogel.

This physical adsorption to the network provides a method of delaying release of the macromolecule in a manner that depends largely on degradation of the hydrogel network. For example, when such a material is injected into a host where proteolytic enzymes are present, the peptide hydrogel can be expected to biodegrade and release the remaining load that is adsorbed to the fibrils in the network into the surrounding tissues.

Effect of Syringe Delivery on Hydrogel Rigidity and Protein Release

A successful drug delivery vehicle should not only be biocompatible, non-damaging to the therapeutic, and have controlled and predictable release profiles, but must also be easily administered with little discomfort to the patient. A minimally invasive method of delivery is via syringe injection. HPL8 hydrogels exhibit shear-thinning behavior under applied stress, but can quickly recover upon the cessation of stress, making them suitable injectable materials. The ability of the 1 wt % HPL8 hydrogel to shear-thin and recover was assessed by oscillatory rheology.

Figure 10:
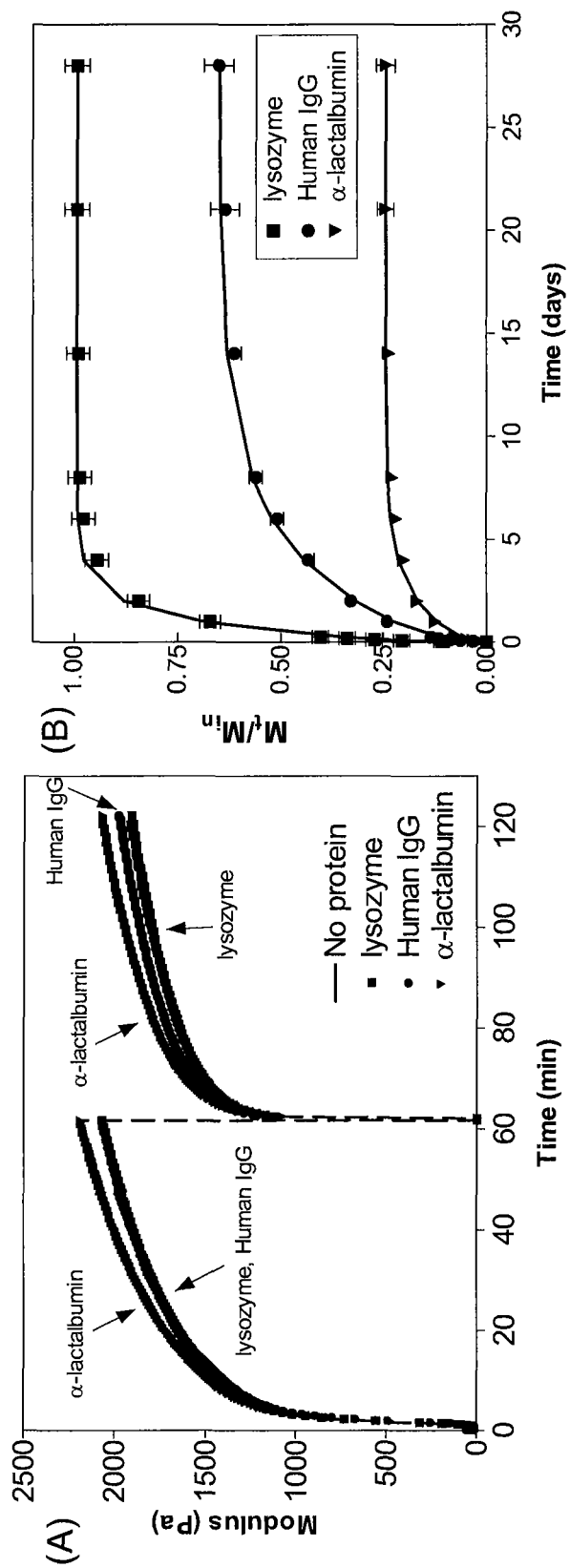
FIG. 10(A) shows dynamic oscillatory time sweeps of 1 wt % HPL8 in physiological buffer at 37° C., alone and also in the presence of α-lactalbumin, lysozyme, and Human IgG.
FIG. 10(B) shows cumulative release profiles ($M_t/M_{in}$) of proteins from 1 wt % HPL8 hydrogels in physiological buffer at 37° C. that were sheared through a syringe needle into a glass vial.

FIG. 10(A) shows dynamic oscillatory time sweeps of 1 wt % HPL8 in physiological buffer at 37° C., alone and also in the presence of α-lactalbumin, lysozyme, and Human IgG. These experiments were conducted to assess if the proteins affected the shear-thinning capability of the HPL8 gels, and if the effect was a function of protein size or charge. The proteins were present during the self-assembly of the peptide hydrogels. Storage modulus was monitored for an hour, as in FIG. 7. To mimic the delivery of the gel through a syringe needle, a strain of 1000% was applied to the material for 30 seconds to convert it to a low viscosity gel. When the high strain was removed, the material instantaneously recovered its mechanical integrity (~60% within the first few seconds) and after an hour, had a storage modulus that was 90% of the value prior to the shearing event.

The plots in FIG. 10(A) demonstrate that the incorporated proteins did not disturb the restructuring of the physically crosslinked material after shear was removed, irrespective of the protein structure. The resultant gels displayed near quantitative recovery of their storage modulus (>90%) after one hour, similar to HPL8 hydrogel alone.

It was considered of interest to determine the effect of syringe delivery on the release profiles of the proteins. This is because of the hypothetical possibility that, during the reorganization of the material, protein might leak from the gel, resulting in a burst release, or might become more physically entrapped within the network, retarding its mobility. Therefore, HPL8 hydrogels in the presence of lysozyme, α-lactalbumin, and human IgG were each formed directly in a syringe and allowed to cure for 1.5 hours. The gels were then syringe-delivered to a glass vial and allowed to recover for 1.5 hours, after which buffer was added to the top of the gels and the bulk release of the proteins was measured as a function of time. FIG. 10(B) shows cumulative release profiles ($M_t/M_{in}$) of proteins from 1 wt % HPL8 hydrogels in physiological buffer at 37° C.

The three proteins displayed the same release profiles as for the gels formed in situ. The greatest amount released was for lysozyme (99%), followed by human IgG (65%). Approximately 75% of the α-lactalbumin was retained in the hydrogel after 28 days. Table 5 shows the diffusion coefficients as determined by Equation 1. The Unreleased Amounts indicate percent of protein remaining in hydrogels after 28 days release time. Comparing the diffusion coefficients and percents retained of the proteins in these experiments with those in the non-sheared gels (Table 4), there was no difference in the release profiles of the small positively charged protein (lysozyme) and the large antibody.

TABLE 5

| Protein | Diffusion Coefficient ($10^{-8}$ cm$^2$/sec) | Unreleased Amount (%) |
|---|---|---|
| Lysozyme | 29 ± 4 | 1 ± 3 |
| Human IgG | 7 ± 1 | 35 ± 4 |
| α-lactalbumin | 14 ± 2 | 75 ± 2 |

In stark contrast, the small negatively charged α-lactalbumin had a greatly reduced diffusion coefficient (less than 50%) but nonetheless also retained to a significantly lower level in the network than was seen for the in situ formed gels. It is apparent that the shearing and reforming of the gels changed their structure and properties, although the exact reasons for this are not immediately apparent. It is also remarkable that this occurred without substantial changes in the bulk Theological experiments, which would normally be expected to reflect any changes in mesh size, which affects diffusion and release. In some embodiments of the invention, these unexpected differences provide a suitable means of modulating release of anionic macromolecules from MAX hydrogels.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A hydrogel for delayed release of an anionic macromolecule, comprising the anionic macromolecule and a peptide in an aqueous medium at a pH of 7.4, wherein the anionic macromolecule has an isoelectric point of at most 6.8, wherein the anionic macromolecule is an anionic protein, wherein the peptide is selected from the group consisting of SEQ ID NO:1 through SEQ ID NO:33, and wherein peptide is present in an amount effective to retain at least 25% of the anionic macromolecule after 28-day extraction of the hydrogel at 37° C. with a pH=7.4 BTP buffer containing 150 mM NaCl.

2. The hydrogel of claim 1, wherein the isoelectric point is at most 6.0.

3. The hydrogel of claim 1, wherein the isoelectric point is at most 5.5.

4. The hydrogel of claim 1, wherein the anionic macromolecule has a molecular weight of at least 10 kD.

5. The hydrogel of claim 1, wherein the anionic macromolecule has a molecular weight of at least 20 kD.

6. The hydrogel of claim 1, wherein the anionic macromolecule has a diffusion coefficient in the hydrogel of at most $60 \times 10^{-8}$ cm$^2$/sec.

7. The hydrogel of claim 1, wherein the anionic macromolecule has a diffusion coefficient in the hydrogel of at most $30 \times 10^{-8}$ cm$^2$/sec.

8. The hydrogel of claim 1, wherein the hydrogel is capable of retaining at least 50% of the anionic macromolecule.

9. The hydrogel of claim 1, wherein the hydrogel is capable of retaining at least 75% of the anionic macromolecule.

10. The hydrogel of claim 1, wherein the peptide is MAX1 (SEQ ID NO:6).

11. The hydrogel of claim 1, wherein the peptide is HPL8 (SEQ ID NO:4).

12. A modified-release hydrogel prepared by a method comprising shearing the hydrogel of claim 1 under conditions sufficient to at least partially shear-thin the gel structure thereof, and subsequently allowing gelation to occur so as to form the modified-release hydrogel, wherein the diffusion coefficient of the anionic macromolecule in the modified-release hydrogel is less than the diffusion coefficient of the anionic macromolecule in the hydrogel of claim 1.

13. The modified-release hydrogel of claim 12, wherein the diffusion coefficient of the anionic macromolecule in the modified-release hydrogel is less than 70% of that of the anionic macromolecule in the hydrogel of claim 1.

14. The modified-release hydrogel of claim 12, wherein the modified-release hydrogel is able to retain less of the anionic macromolecule after 28-day extraction at 37° C. with a pH=7.4 BTP buffer containing 150 mM NaCl than the hydrogel of claim 1 is able to retain.

15. A method of introducing an anionic macromolecule to an animal, comprising the step of introducing the hydrogel of claim 1 into the body of an animal.

16. The method of claim 15, further comprising a step of shearing the hydrogel prior to introducing it into the body of the animal.

17. The method of claim 16, wherein the shearing results from injection into the animal through a syringe needle.

18. A method of introducing an anionic macromolecule to an animal, comprising the step of introducing the modified-release hydrogel of claim 12 into the body of an animal.

* * * * *

SEQUENCE LISTING

<160> NUMBER OF SEQ ID NOS: 33

<210> SEQ ID NO 1
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated

<400> SEQUENCE: 1

Val Lys Val Lys Val Lys Val Lys Val Pro Pro Thr Lys Val Lys Val
1               5                   10                  15

Lys Val Lys Val
            20

<210> SEQ ID NO 2
<211> LENGTH: 20
<212> TYPE: PRT

```
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated

<400> SEQUENCE: 2

Val Lys Val Lys Val Lys Val Lys Tyr Asn Gly Thr Lys Val Lys Val
1               5                   10                  15

Lys Val Lys Val
            20

<210> SEQ ID NO 3
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated

<400> SEQUENCE: 3

Val Lys Val Lys Val Lys Val Lys Val Arg Gly Asp Lys Val Lys Val
1               5                   10                  15

Lys Val Lys Val
            20

<210> SEQ ID NO 4
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 4

Val Lys Val Lys Val Lys Val Lys Pro Pro Thr Lys Val Glu Val
1               5                   10                  15

Lys Val Lys Val
            20

<210> SEQ ID NO 5
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: Terminal COOH group is NH2-amidated

<400> SEQUENCE: 5

Val Lys Tyr Asn Gly Thr Lys Val
1               5

<210> SEQ ID NO 6
```

```
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 6

Val Lys Val Lys Val Lys Val Lys Val Pro Pro Thr Lys Val Lys Val
1               5                   10                  15

Lys Val Lys Val
            20

<210> SEQ ID NO 7
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 7

Val Lys Val Lys Val Lys Val Lys Val Pro Pro Thr Lys Val Lys Thr
1               5                   10                  15

Lys Val Lys Val
            20

<210> SEQ ID NO 8
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 8

Val Lys Val Lys Val Lys Thr Lys Val Pro Pro Thr Lys Val Lys Thr
1               5                   10                  15

Lys Val Lys Val
            20

<210> SEQ ID NO 9
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
```

```
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 9

Lys Val Lys Val Lys Val Lys Val Lys Pro Pro Ser Val Lys Val Lys
1               5                   10                  15

Val Lys Val Lys
            20

<210> SEQ ID NO 10
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 10

Val Lys Val Lys Val Lys Val Lys Val Pro Pro Thr Lys Val Lys Glu
1               5                   10                  15

Lys Val Lys Val
            20

<210> SEQ ID NO 11
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 11

Val Lys Val Lys Val Lys Val Lys Val Pro Pro Thr Lys Val Lys Cys
1               5                   10                  15

Lys Val Lys Val
            20

<210> SEQ ID NO 12
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline
```

```
<400> SEQUENCE: 12

Val Lys Val Lys Val Lys Val Lys Val Pro Gly Thr Lys Val Lys Val
1               5                   10                  15

Lys Val Lys Val
            20

<210> SEQ ID NO 13
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (11)..(11)
<223> OTHER INFORMATION: Pro is D-Proline

<400> SEQUENCE: 13

Val Lys Val Lys Val Lys Val Lys Val Pro Pro Thr Lys Val Lys Val
1               5                   10                  15

Lys Val Lys Val
            20

<210> SEQ ID NO 14
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline
<220> FEATURE:
<221> NAME/KEY: MISC_FEATURE
<222> LOCATION: (11)..(11)
<223> OTHER INFORMATION: Pro is D-Proline

<400> SEQUENCE: 14

Val Lys Val Lys Val Lys Val Lys Val Pro Pro Thr Lys Val Lys Val
1               5                   10                  15

Lys Val Lys Val
            20

<210> SEQ ID NO 15
<211> LENGTH: 19
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (19)
<223> OTHER INFORMATION: Terminal COOH group is NH2-amidated
<220> FEATURE:
<221> NAME/KEY: MISC_FEATURE
<222> LOCATION: (9)..(9)
<223> OTHER INFORMATION: Pro is D-Proline

<400> SEQUENCE: 15

Val Lys Val Lys Lys Cys Lys Val Pro Pro Thr Lys Val Lys Cys Lys
```

Val Lys Val

<210> SEQ ID NO 16
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 16

Val Lys Val Lys Cys Lys Val Lys Val Pro Pro Thr Lys Val Cys Val
1               5                   10                  15

Lys Val Lys Val
            20

<210> SEQ ID NO 17
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 17

Val Lys Val Lys Val Cys Val Lys Val Pro Pro Thr Cys Val Lys Val
1               5                   10                  15

Lys Val Lys Val
            20

<210> SEQ ID NO 18
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 18

Val Lys Val Lys Val Cys Val Lys Val Pro Pro Thr Lys Val Lys Val
1               5                   10                  15

Cys Val Lys Val
            20

<210> SEQ ID NO 19
<211> LENGTH: 20

```
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 19

Val Lys Val Lys Val Lys Val Cys Val Pro Pro Thr Lys Val Lys Val
1               5                   10                  15

Cys Val Lys Val
            20

<210> SEQ ID NO 20
<211> LENGTH: 26
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (26)
<223> OTHER INFORMATION: Terminal COOH group is NH2-amidated
<220> FEATURE:
<221> NAME/KEY: MISC_FEATURE
<222> LOCATION: (13)..(13)
<223> OTHER INFORMATION: Pro is D-Proline

<400> SEQUENCE: 20

Arg Gly Asp Val Lys Val Lys Val Lys Val Lys Val Pro Pro Thr Lys
1               5                   10                  15

Val Lys Val Lys Val Lys Val Arg Gly Asp
            20                  25

<210> SEQ ID NO 21
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 21

Val Lys Val Glu Val Lys Val Glu Val Pro Pro Thr Lys Val Glu Val
1               5                   10                  15

Lys Val Glu Val
            20

<210> SEQ ID NO 22
<211> LENGTH: 24
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (24)
```

```
<223> OTHER INFORMATION: Terminal COOH group is NH2-amidated
<220> FEATURE:
<221> NAME/KEY: MISC_FEATURE
<222> LOCATION: (12)..(12)
<223> OTHER INFORMATION: Pro is D-Proline

<400> SEQUENCE: 22

Val Lys Val Lys Val Lys Val Lys Val Lys Val Pro Pro Thr Lys Val
 1               5                  10                  15

Lys Val Lys Val Lys Val Lys Val
            20

<210> SEQ ID NO 23
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (16)
<223> OTHER INFORMATION: Terminal COOH group is NH2-amidated
<220> FEATURE:
<221> NAME/KEY: MISC_FEATURE
<222> LOCATION: (8)..(8)
<223> OTHER INFORMATION: Pro is D-Proline

<400> SEQUENCE: 23

Val Lys Val Lys Val Lys Val Pro Pro Thr Lys Val Lys Val Lys Val
 1               5                  10                  15

<210> SEQ ID NO 24
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline
<220> FEATURE:
<221> NAME/KEY: MISC_FEATURE
<222> LOCATION: (2), (4), (6), (8), (13), (15), (17), (19)
<223> OTHER INFORMATION: Xaa is Ornithine

<400> SEQUENCE: 24

Val Xaa Val Xaa Val Xaa Val Xaa Val Pro Pro Thr Xaa Val Xaa Val
 1               5                  10                  15

Xaa Val Xaa Val
            20

<210> SEQ ID NO 25
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline
<220> FEATURE:
```

```
<221> NAME/KEY: MISC_FEATURE
<222> LOCATION: (2), (4), (6), (8), (13), (15), (17), (19)
<223> OTHER INFORMATION: Xaa is Diaminobutyric acid

<400> SEQUENCE: 25

Val Xaa Val Xaa Val Xaa Val Xaa Val Pro Pro Thr Xaa Val Xaa Val
1               5                   10                  15

Xaa Val Xaa Val
        20

<210> SEQ ID NO 26
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (2), (4), (6), (8), (13), (15), (17), (19)
<223> OTHER INFORMATION: Xaa is diaminopropionic acid
<220> FEATURE:
<221> NAME/KEY: MISC_FEATURE
<222> LOCATION: (10)..(10)
<223> OTHER INFORMATION: Pro is D-Proline

<400> SEQUENCE: 26

Val Xaa Val Xaa Val Xaa Val Xaa Val Pro Pro Thr Xaa Val Xaa Val
1               5                   10                  15

Xaa Val Xaa Val
        20

<210> SEQ ID NO 27
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 27

Val Arg Val Arg Val Arg Val Arg Val Pro Pro Thr Arg Val Arg Val
1               5                   10                  15

Arg Val Arg Val
        20

<210> SEQ ID NO 28
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (1), (3), (5), (7), (14), (16), (18), (20)
<223> OTHER INFORMATION: Xaa is aminoisobutyric acid
```

<220> FEATURE:
<221> NAME/KEY: MISC_FEATURE
<222> LOCATION: (10)..(10)
<223> OTHER INFORMATION: Pro is D-Proline

<400> SEQUENCE: 28

Xaa Lys Xaa Lys Xaa Lys Xaa Lys Val Pro Pro Thr Lys Xaa Lys Xaa
1               5                   10                  15

Lys Xaa Lys Xaa
            20

<210> SEQ ID NO 29
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline
<220> FEATURE:
<221> NAME/KEY: MISC_FEATURE
<222> LOCATION: (1), (3), (5), (7), (14), (16), (18), (20)
<223> OTHER INFORMATION: Xaa is Norvaline

<400> SEQUENCE: 29

Xaa Lys Xaa Lys Xaa Lys Xaa Lys Val Pro Pro Thr Lys Xaa Lys Xaa
1               5                   10                  15

Lys Xaa Lys Xaa
            20

<210> SEQ ID NO 30
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline
<220> FEATURE:
<221> NAME/KEY: MISC_FEATURE
<222> LOCATION: (1), (3), (5), (7), (14), (16), (18), (20)
<223> OTHER INFORMATION: Xaa is Norleucine

<400> SEQUENCE: 30

Xaa Lys Xaa Lys Xaa Lys Xaa Lys Val Pro Pro Thr Lys Xaa Lys Xaa
1               5                   10                  15

Lys Xaa Lys Xaa
            20

<210> SEQ ID NO 31
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)

```
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 31

Phe Lys Phe Lys Phe Lys Phe Lys Val Pro Pro Thr Lys Phe Lys Phe
1               5                   10                  15

Lys Phe Lys Phe
            20

<210> SEQ ID NO 32
<211> LENGTH: 20
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (20)
<223> OTHER INFORMATION: Terminal COOH group is NH2-amidated
<220> FEATURE:
<221> NAME/KEY: MISC_FEATURE
<222> LOCATION: (10)..(10)
<223> OTHER INFORMATION: Pro is D-Proline

<400> SEQUENCE: 32

Ile Lys Ile Lys Ile Lys Ile Lys Val Pro Pro Thr Lys Ile Lys Ile
1               5                   10                  15

Lys Ile Lys Ile
            20

<210> SEQ ID NO 33
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: Terminal COOH group is NH2-amidated
<220> FEATURE:
<221> NAME/KEY: MISC_FEATURE
<222> LOCATION: (4)..(4)
<223> OTHER INFORMATION: Pro is D-Proline

<400> SEQUENCE: 33

Val Lys Val Pro Pro Thr Lys Val
1               5
```